US009265475B2

(12) United States Patent
Yang et al.

(10) Patent No.: US 9,265,475 B2
(45) Date of Patent: *Feb. 23, 2016

(54) METHODS AND APPARATUS FOR SCATTER CORRECTION FOR CBCT SYSTEM AND CONE-BEAM IMAGE RECONSTRUCTION

(71) Applicant: Carestream Health, Inc., Rochester, NY (US)

(72) Inventors: Dong Yang, Rochester, NY (US); Nathan J. Packard, Rochester, NY (US); Robert A. Senn, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/337,707

(22) Filed: Jul. 22, 2014

(65) Prior Publication Data

US 2014/0334700 A1  Nov. 13, 2014

Related U.S. Application Data

(63) Continuation of application No. 13/537,226, filed on Jun. 29, 2012, now Pat. No. 8,818,065.

(60) Provisional application No. 61/503,632, filed on Jul. 1, 2011.

(51) Int. Cl.
| G06K 9/00 | (2006.01) |
| A61B 6/00 | (2006.01) |
| G06T 11/00 | (2006.01) |
| A61B 6/03 | (2006.01) |
| G06T 5/50 | (2006.01) |
| G06T 7/00 | (2006.01) |

(52) U.S. Cl.
CPC ............... *A61B 6/5282* (2013.01); *A61B 6/032* (2013.01); *A61B 6/4085* (2013.01); *A61B 6/583* (2013.01); *G06T 5/50* (2013.01); *G06T 7/0016* (2013.01); *G06T 11/005* (2013.01); *G06T 2207/10116* (2013.01); *G06T 2207/20182* (2013.01)

(58) Field of Classification Search
None
See application file for complete search history.

(56) References Cited

U.S. PATENT DOCUMENTS

| 5,270,926 | A | 12/1993 | Tam | |
| 5,999,587 | A | 12/1999 | Ning et al. | |
| 6,480,565 | B1 | 11/2002 | Ning | |
| 6,687,326 | B1 * | 2/2004 | Bechwati et al. | 378/7 |
| 7,551,716 | B2 | 6/2009 | Rührnschopf | |
| 2004/0202360 | A1 | 10/2004 | Besson | |
| 2007/0104310 | A1 | 5/2007 | Nottling et al. | |
| 2008/0080663 | A1 | 4/2008 | Haerer et al. | |
| 2008/0253515 | A1 | 10/2008 | Bertram et al. | |

(Continued)

*Primary Examiner* — Atiba O Fitzpatrick

(57) ABSTRACT

Embodiments of methods and/or apparatus for 3-D volume image reconstruction of a subject, executed at least in part on a computer for use with a digital radiographic apparatus, can obtain image data for 2-D projection images over a range of scan angles. For each of the plurality of projection images, an enhanced projection image can be generated. In one embodiment, a first scatter intensity distribution through the plurality of projection images can be modulated based on a first scaling function and a SPR to generate a second scatter intensity distribution through the plurality of projection images, which can be combined with the original plurality of projection images.

24 Claims, 23 Drawing Sheets

(56) References Cited

U.S. PATENT DOCUMENTS

| | | |
|---|---|---|
| 2009/0135993 A1 | 5/2009 | Harer et al. |
| 2009/0225932 A1 | 9/2009 | Zhu et al. |
| 2009/0290682 A1 | 11/2009 | Star-Lack et al. |
| 2010/0014730 A1 | 1/2010 | Hahn et al. |
| 2010/0046705 A1 | 2/2010 | Jabri et al. |
| 2010/0158335 A1 | 6/2010 | Ning et al. |
| 2010/0189376 A1 | 7/2010 | Bertram et al. |
| 2014/0037044 A1* | 2/2014 | Ning et al. .................. 378/4 |

* cited by examiner

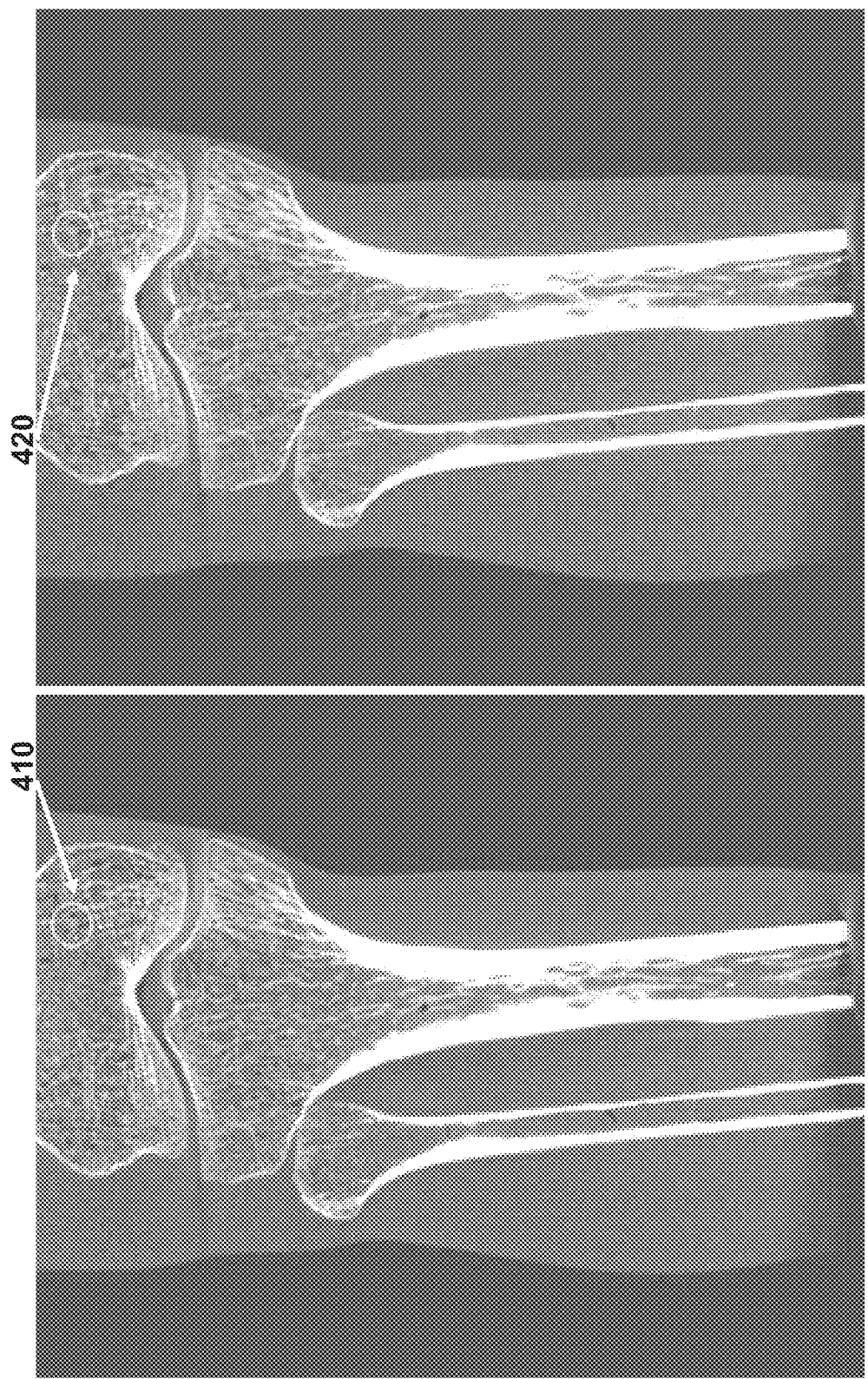

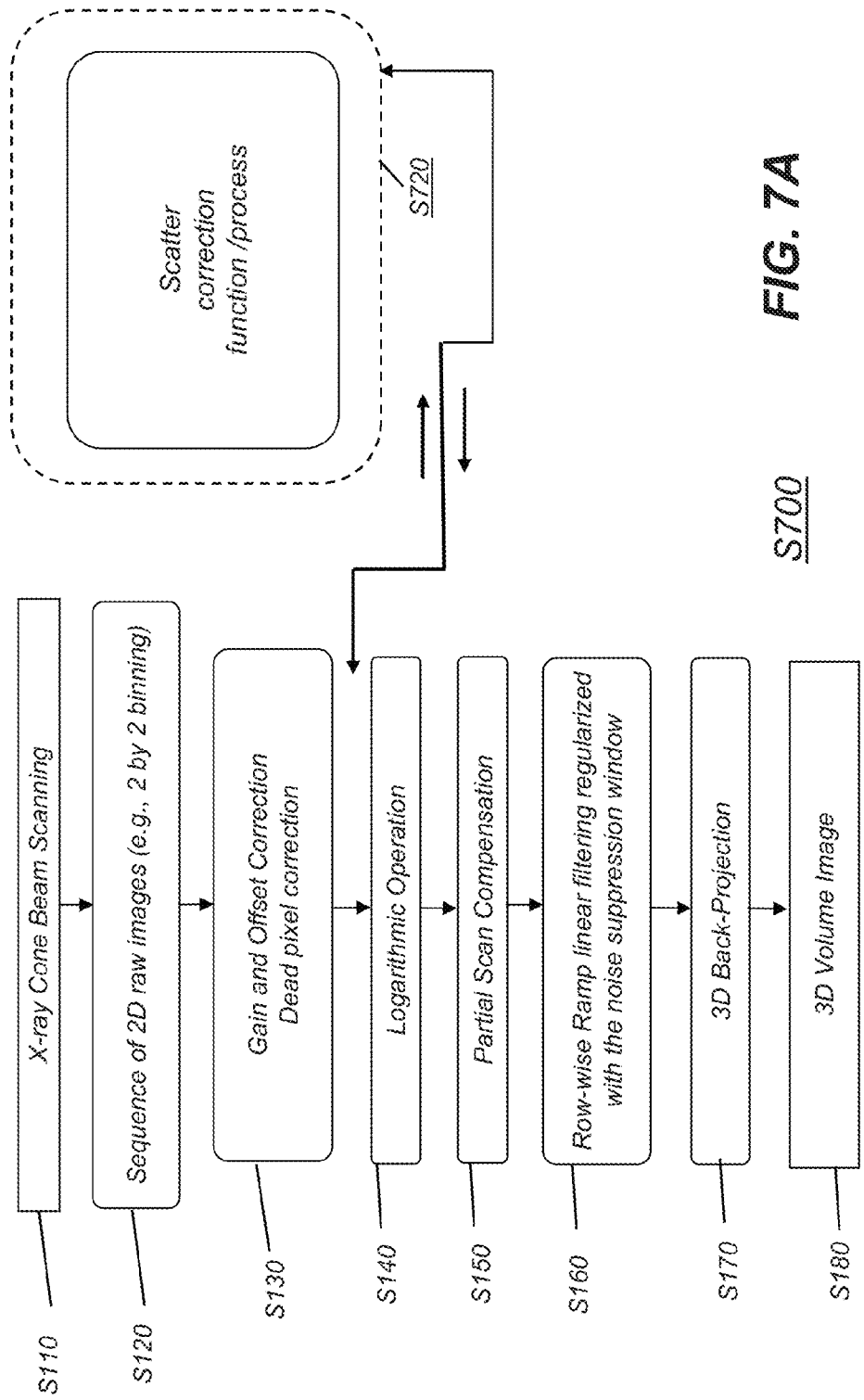

METHODS AND APPARATUS FOR SCATTER CORRECTION FOR CBCT SYSTEM AND CONE-BEAM IMAGE RECONSTRUCTION

CROSS-REFERENCE TO RELATED APPLICATIONS

This application is a continuation of U.S. patent application Ser. No. 13/537,226, filed Jun. 29, 2012, which claimed the benefit of U.S. Provisional Application No. 61/503,632, filed Jul. 1, 2011, entitled METHODS AND APPARATUS FOR SCATTER CORRECTION FOR CBCT SYSTEM AND CONE-BEAM IMAGE RECONSTRUCTION, which is hereby incorporated by reference in its entirety.

FIELD OF THE INVENTION

Embodiments described herein relate generally to radiation-based imaging. More particularly, the described embodiments relate to the estimation of scatter radiation within projection images. Exemplary embodiments relate to the field of digital radiography, diagnostic imaging and more particularly to Cone-Beam Computed Tomography (CBCT) imaging. More specifically, the application relates to methods and apparatus for improved scatter correction, for example, in projection data of CBCT image content.

BACKGROUND OF THE INVENTION

Cone-beam computed tomography or CBCT scanning makes it possible to improve image capture and processing speeds by directing a cone-beam source through the patient or other subject to obtain an image on a flat-panel X-ray detector. In cone-beam computed tomography scanning, a volume or 3-D image is reconstructed from numerous individual scan projections, each taken at a different angle, whose image data is aligned and processed in order to generate and present data as a collection of volume pixels or voxels.

Generation of scatter in X-ray radiographic and flat panel based CT imaging is very complex. Incident X-ray photons are scattered inside the object, and when scattered photons reach the detector, an overestimation of the registered total intensity in each projection, which can be equivalent to an underestimation of attenuation coefficients associated with the materials inside the object, can result. Scatter may lead to image artifacts such as "cupping" in homogeneous object or dark streaks between image regions of high attenuation. As a result of the contamination of collected data with scattered photons, the low-contrast detectability of a CBCT system is decreased.

Related art scatter correction methods can include hardware scatter rejection (e.g., systems equipped with bowtie filter and/or anti-scatter grids), measurement of scatter using beam stop methods, or image processing methods (e.g., software applications) such as Monte Carlo modeling of photon transport through the patient, convolution-superposition methods, analytical scatter models, heuristic methods based on approximate geometry; or image enhancement methods.

Cone-beam computed tomography (CBCT) scanning is of significant interest for applications such as biomedical, dental, and industrial applications.

Improved scatter correction or image processing methods of scatter correction on projection images that can reduce artifacts in the reconstructed image domain is desirable. There is a compelling need for improved methods for scatter correction in volume imaging techniques.

SUMMARY OF THE INVENTION

Accordingly, it is an aspect of this application to address in whole or in part, at least the foregoing and other deficiencies in the related art. It is another aspect of this application to provide in whole or in part, at least the advantages described herein.

Another aspect of this application is to provide methods and/or systems that can address scatter correction in volume DR image reconstruction processing such as CBCT volume DR image reconstruction.

These objects are given only by way of illustrative example, and such objects may be exemplary of one or more embodiments of the application. Other desirable objectives and advantages inherently achieved by the disclosed embodiments or combinations thereof may occur or become apparent to those skilled in the art. The invention is defined by the appended claims.

According to one embodiment of the invention, there is provided a method for digital radiographic 3D volume image reconstruction of a subject, executed at least in part on a computer.

According to one embodiment of the invention, there is provided a method for digital radiographic 3D volume image reconstruction of a subject, executed at least in part on a computer, that can include obtaining image data for a plurality of 2D projection images over a range of scan angles; generating, for each of the plurality of 2D projection images, a first scatter intensity distribution by estimating a first scatter distribution in an air region from at least one 2D current projection image, segmenting the at least one 2D current projection image to determine an object shadow portion, and determining a coarse scatter intensity within the object shadow portion based on an interpolation of the first scatter distribution; generating, for said each of the plurality of 2D projection images, a second scatter intensity distribution for the 2D projection image by: modulating the first scatter intensity distribution for the plurality of 2D projection images by a rescaled processed object intensity in log space, where the modulating includes determining a first scaling factor for at least one point in the range of scan angles that occurs within the object shadow portion using a scatter-to-primary ratio, determining a moderating function based on the first scaling function, and applying the moderating function to the plurality of first scatter intensity distributions for the plurality of 2D projection images to generate the plurality of second scatter intensity distribution for the plurality of 2D projection images for the range of scan angles, and combining the plurality of second scatter intensity distribution for the plurality of 2D projection images to the plurality of 2D projection images to determine a plurality of scatter corrected 2D projection images; and storing the scatter corrected plurality of 2D projection images in a computer-accessible memory.

According to one embodiment of the invention, there is provided a digital radiography CBCT imaging system for digital radiographic 3D volume image reconstruction of a subject.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 4A-4H are diagrams that show exemplary knee phantom axial and coronal images, respectively, under different scatter correction scenarios.

FIGS. 7A-7B include a logic flow diagram that shows a sequence of processes used for 3-D volume image processing according to one embodiment of the application.

DESCRIPTION OF EXEMPLARY EMBODIMENTS

Figure 1:
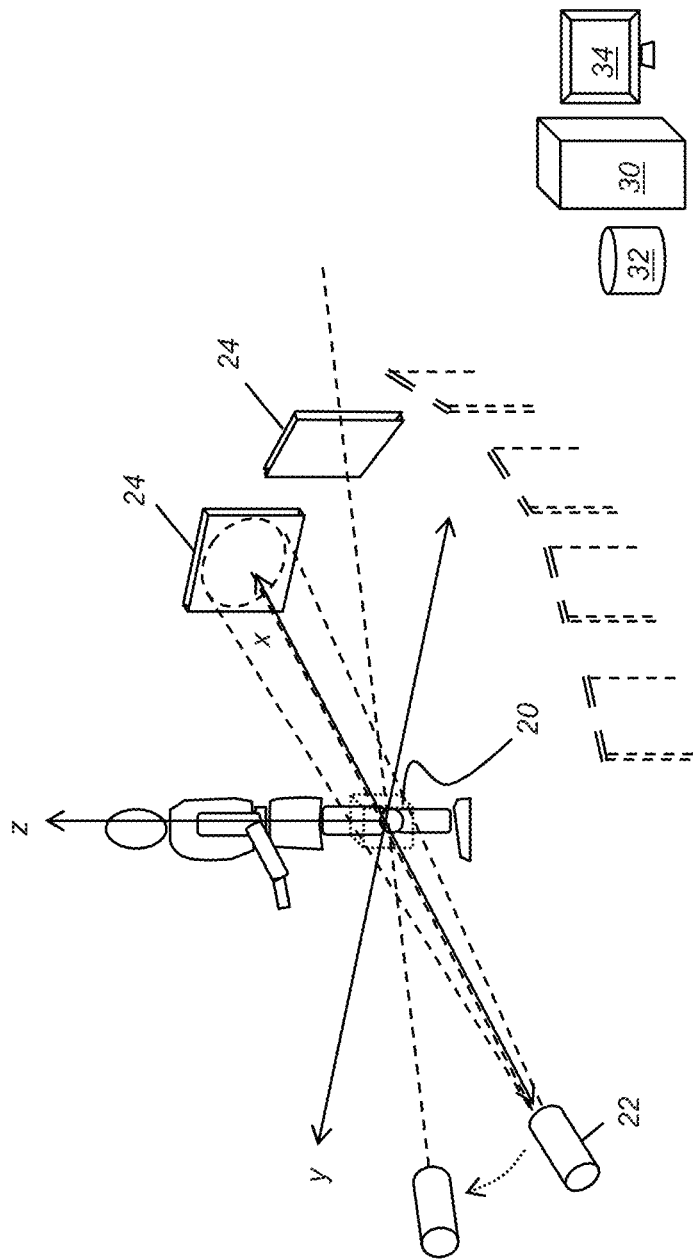
FIG. 1 is a schematic diagram showing components and architecture used for conventional CBCT scanning

The following is a description of exemplary embodiments according to the application, reference being made to the drawings in which the same reference numerals identify the same elements of structure in each of the several figures, and similar descriptions concerning components and arrangement or interaction of components already described are omitted. Where they are used, the terms "first", "second", and so on, do not necessarily denote any ordinal or priority relation, but may simply be used to more clearly distinguish one element from another.

In the context of the present disclosure, the term "code value" refers to the value that is associated with each volume image data element or voxel in the reconstructed 3-D volume image. The code values for CT images are often, but not always, expressed in Hounsfield units (HU).

CBCT imaging apparatus and imaging algorithms used to obtain 3-D volume images using such systems are well known in the diagnostic imaging art and are, therefore, not described in detail in the present application. Some exemplary algorithms for forming 3-D volume images from the source 2-D images, projection images that are obtained in operation of the CBCT imaging apparatus can be found, for example, in U.S. Pat. No. 5,999,587 entitled "Method of and System for Cone-Beam Tomography Reconstruction" to Ning et al. and in U.S. Pat. No. 5,270,926 entitled "Method and Apparatus for Reconstructing a Three-Dimensional Computerized Tomography (CT) Image of an Object from Incomplete Cone Beam Data" to Tam.

In typical applications, a computer or other type of dedicated logic processor for obtaining, processing, and storing image data is part of the CBCT system, along with one or more displays for viewing image results. A computer-accessible memory is also provided, which may be a non-volatile memory storage device used for longer term storage, such as a device using magnetic, optical, or other data storage media. In addition, the computer-accessible memory can comprise an electronic memory such as a random access memory (RAM) that is used as volatile memory for shorter term data storage, such as memory used as a workspace for operating upon data or used in conjunction with a display device for temporarily storing image content as a display buffer, or memory that is employed to store a computer program having instructions for controlling one or more computers to practice method and/or system embodiments according to the present application.

To understand exemplary methods and/or apparatus embodiments according to the present application and problems addressed by embodiments, it is instructive to review principles and terminology used for CBCT image capture and reconstruction. Referring to the perspective view of FIG. 1, there is shown, in schematic form and using exaggerated distances for clarity of description, the activity of an exemplary conventional CBCT imaging apparatus for obtaining the individual 2-D images that are used to form a 3-D volume image. A cone-beam radiation source 22 directs a cone of radiation toward a subject 20, such as a patient or other imaged subject. A sequence of images of subject 20 is obtained in rapid succession at varying angles about the subject over a range of scan angles, such as one image at each 1-degree angle increment in a 200-degree orbit. A DR detector 24 is moved to different imaging positions about subject 20 in concert with corresponding movement of radiation source 22. For example, such corresponding movement can have a prescribed 2D or 3D relationship. FIG. 1 shows a representative sampling of DR detector 24 positions to illustrate how these images are obtained relative to the position of subject 20. Once the needed 2-D projection images are captured in a prescribed sequence, a suitable imaging algorithm, such as FDK filtered back projection or other conventional technique, can be used for generating the 3-D volume image. Image acquisition and program execution are performed by a computer 30 or by a networked group of computers 30 that are in image data communication with DR detectors 24. Image processing and storage is performed using a computer-accessible memory in image data communication with DR detectors 24 such as computer-accessible memory 32. The 3-D volume image or exemplary 2-D image data can be presented on a display 34.

Figure 2:
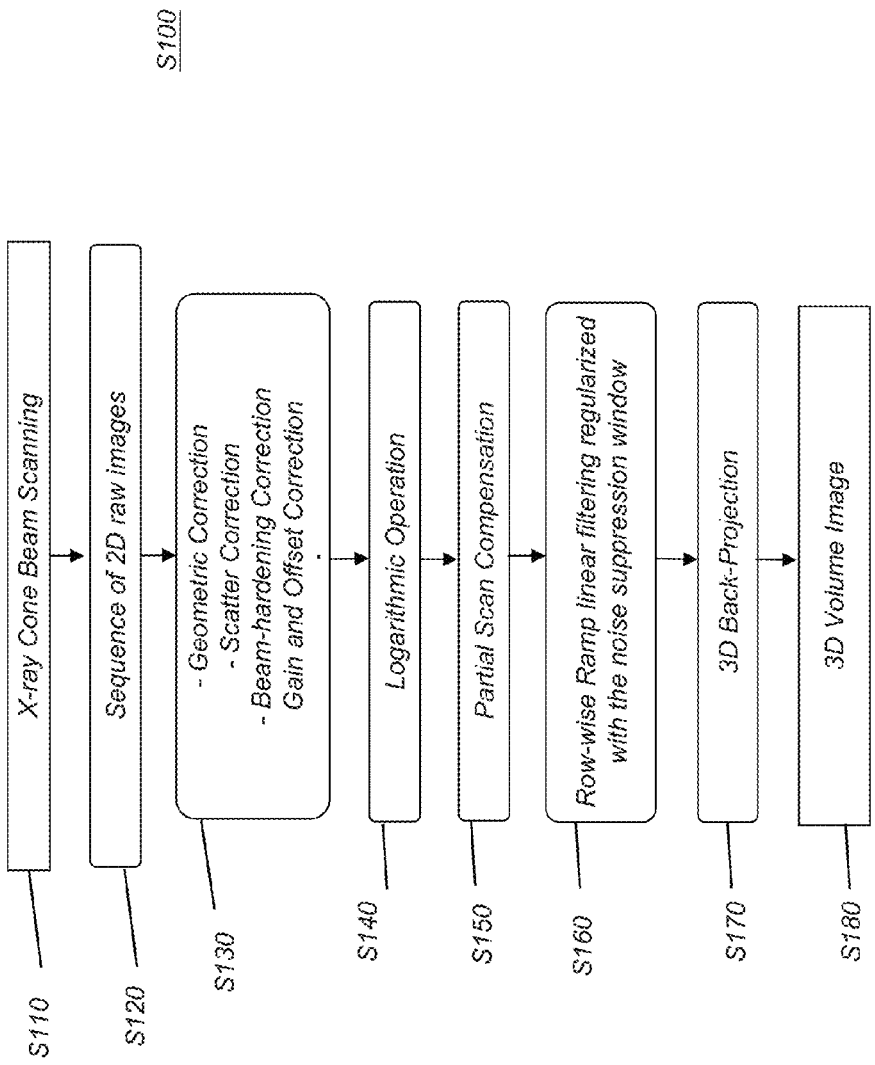
FIG. 2 is a logic flow diagram showing the sequence of processes used for conventional CBCT volume image reconstruction.

The logic flow diagram of FIG. 2 shows a conventional image processing sequence S100 for CBCT reconstruction using partial scans. A scanning step S110 directs cone beam exposure toward the subject, enabling collection of a sequence of 2-D raw data images for projection over a range of angles in an image data acquisition step S120. An image correction step S130 then performs standard processing of the projection images such as but not limited to geometric correction, scatter correction, gain and offset correction, and beam hardening correction. A logarithmic operation step S140 obtains the line integral data that is used for conventional reconstruction methods, such as the FDK method well-known to those skilled in the volume image reconstruction arts.

An optional partial scan compensation step S150 is then executed when it is necessary to correct for constrained scan data or image truncation and related problems that relate to positioning the detector about the imaged subject throughout the scan orbit. A ramp filtering step S160 follows, providing row-wise linear filtering that is regularized with the noise suppression window in conventional processing. A back projection step S170 is then executed and an image formation step S180 reconstructs the 3-D volume image using one or more of the non-truncation corrected images. FDK processing generally encompasses the procedures of steps S160 and S170. The reconstructed 3-D image can then be stored in a computer-accessible memory and displayed.

Conventional image processing sequence S100 of FIG. 2 has been proven and refined in numerous cases with both phantom and patient images.

As was commonly known, the X-ray path length through tissue at the edges of the field of view (FOV) is typically shortened in relation to the structure of the scanned object, which can result in less attenuation of peripheral scatter and, thus disproportionately increased peripheral scatter contribution to image degradation. A bow tie filter (e.g., copper) is sometimes used to modulate the X-ray beam profile by increasing photon density at the center of the cone and reducing photon density at the periphery. This results in a reduction of the scatter to the area on the detector where the object shadow is projected. However, the related art use of the bow tie filter for scatter reduction requires additional x-ray tube power to generate the equivalent x-ray fluence as when there is no bow tie filter in place. The inventors determined from exemplary CBCT system study that the extra tube power required for the bow tie filter used (e.g., based on the prescribed design) made its use infeasible (e.g., significantly reduced primary X-ray beams and/or caused some unwanted pattern in the reconstructed images).

The use of the anti-scatter grid is recognized to improve the soft tissue contrast and suppress the scatter induced artifacts, however, the anti-scatter grid also can increase noise, which leads to a degradation in overall image quality. Accordingly, an escalation in x-ray dose or a reduction in spatial resolution is needed to offset the increased noise with the implementation of the anti-scatter grid. The spatial resolution loss associated with using the anti-scatter grid is another concern whether the anti-scatter grid should be used at all for an imaging task where high spatial resolution is required. Head skull phantom scans on one embodiment of a CBCT prototype showed that some tiny blood vessel structures could not be resolved (e.g., visible or seen) in the projection image when detector was equipped with anti-scatter grid, as shown in FIG. 3B, however the tiny blood vessel structures could be resolved (e.g., visible or seen) when the detector is not equipped with anti-scatter grid as shown in FIG. 3C, where in both cases the x-ray exposure level was set up the same.

The design of one embodiment of a CBCT system can be compact with the cone angle spanned by the configuration of the X-ray tube and the flat panel detector is 15 degrees and the air gap between the object and the detector is very limited, which can indicate that the scatter is significant associated with scanning geometry. Scatter suppression is a must or preferred for embodiments of CBCT imaging systems according to the application. Further, the use of a bow-tie filter and/or an anti-scatter grid is not preferred or might not be appropriate for certain CBCT applications, and in cases where they are used, additional software scatter corrections can further increase uniformity and reduce artifacts. In certain exemplary embodiments, methods/software for scatter correction schemes should be or must be incorporated to suppress the scatter to achieve the clinically acceptable image quality.

For clinical applications, the development of an efficient scatter correction technique for CBCT imaging system preferably considers at least issues such as patient dose, scanning time and computation complexity. Certain exemplary embodiments described herein provide a novel scatter correction approach for CBCT imaging systems. Exemplary rationale behind the proposed method is that there is a strong correlation between the measurements of the object in the log space (line integral) and the scatter to primary ratio (SPR). In one exemplary embodiment, a process for scatter correction for a CBCT imaging system can be described as follows:

1. Estimating the scatter distribution in the air region by subtraction of the $I_0$ (getting from air calibration scan) from the current projection image $RawOb_i(x, y)$. $i=1, \ldots, N$. N: number of projections.

In one embodiment, the scatter distribution in air can be considered a fixed value, but preferably, the scatter distribution is air can be determined on per frame basis to address and/or compensate for real-time environment changes (e.g., beam energy and/or detector performance e.g., lag).

2. The segmented scatter image in the air region can be used to do interpolation (e.g., linear) to get the coarse scatter intensity within the object shadow, represented as: $SCOb_i(x, y)$. $i=1, \ldots, N$. N: number of projections.

In one embodiment, each frame can be segmented and the scatter in air region can be determined (e.g., by subtracting Io). Then, the course scatter behind the object can be interpolated from the scatter in the at least one segmented air region.

3. This coarse scatter intensity distribution within the object shadow will be modulated by the resealed processed object intensity in log space. In one exemplary embodiment, detailed description of this step can be summarized as:

3.1. Determining the scaling factor: Searching the highest intensity in Log space across all the viewing projection images to get $img_i(x_0, y_0)$, $i \in (1, \ldots, N)$. Based on the value of $img_i(x_0, y_0)$, assume a scatter to primary ratio (spr) (e.g., empirical, historical data). The scaling factor is determined by following equations:

$$\text{Scal\_Factor} = img_i(x_0, y_0)/(1 - \text{Ratio\_Obj}(x_0, y_0)) \quad (1)$$

Where:

$$\text{Ratio\_Obj}(x_0, y_0) = \frac{RawOb_i(x_0, y_0) \cdot spr/(1 + spr)}{SCOb_i(x_0, y_0)} \quad (2)$$

In one embodiment, exemplary process details to determine the Ratio\_Obj($x_0$, $y_0$):

The point $img_i(x_0, y_0)$ in Log space can be where the most attenuated point across the whole scanning views. The corresponding point in the linear space is: $RawOb_i(x_0, y_0)$. Based on the assumed scatter to primary ratio (spr), we have the relationship:

$$RawOb_i(x_0, y_0) = \text{scatter}(x_0, y_0) + \text{primary}(x_0, y_0)$$

$$spr = \text{scatter}(x_0, y_0)/\text{primary}(x_0, y_0)$$

The equation:

$$RawOb_i(x_0, y_0) \cdot spr/(1 + spr) = (s + p) \cdot \frac{s/p}{(1 + s/p)} = (s + p) \cdot \frac{s}{s + p} = s(x_0, y_0)$$

Given the coarse linearly interpolated scatter signal at this same point: $SCOb_i(x_0, y_0)$, we can calculate the Ratio\_Obj $(x_0, y_0)$, which is the percentage of the assumed scatter in the coarse linearly interpolated scatter intensity at this image point $img_i(x_0, y_0)$. This shows a derivation for equation (2).

Because we want to get the scatter modulator based on the projection data in Log space, we have to modify the projection data in Log space to give us this percentage Ratio\_Obj $(x_0, y_0)$ at the image point $img_i(x_0, y_0)$ to determine a scaling factor in Log space data and apply this scaling factor to all projection view data to get the final scatter modulator (e.g., which can be actually the percentage of the scatter intensity in the object shadow in the coarse linearly interpolated scatter intensity). At the point $img_i(x_0, y_0)$, Ratio_Obj$(x_0, y_0)$ has been determined, and we also know that Ratio_Obj$(x_0, y_0)$ is the smallest and value at the point $img_i(x_0, y_0)$ is the largest across all the image views. In order to determine a scaling factor, we have to have the value at image point $img_i(x_0, y_0)$ divided by a scaling factor and subtracted from 1 to get the percentage defined as Ratio_Obj$(x_0, y_0)$. Mathematically, it can be represented by:

$$\text{Ratio\_Obj}(x_0, y_0) = 1 - \frac{img_i(x_0, y_0)}{\text{Scal\_Factor}}$$

Then we can solve scaling factor mathematically by:

Scal_Factor=$img_i(x_0,y_0)/(1-\text{Ratio\_Obj}(x_0,y_0))$

This shows a derivation for equation (1).

3.2. Determining the modulator: all the projections are to be divided by this globally determined scaling factor to get inverted scaled projection as:

$$\text{InvPRO}_i(x, y) = 1 - \frac{img_i(x, y)}{\text{Scal\_Factor}}$$

and this inverted scaled projection can preferably be apodized by an over-correction compensation function to compensate the over correction at the boundary part of the object. This function can be row-wise dependent in each projection image, and the position of the peak of this function, which can be 1 where the highest value of same row in projection image. The distance from this peak to each side of the object can be parameterized to constitute this function using Gaussian equation. So the final modulator is:

Modulator$_i(x,y)$=InvPRO$_i(x,y)$·OcComp$_i(x,y)$ 3.3. The final estimated scatter intensity within the object shadow is:

EstScOb$_i(x,y)$=SCOb$_i(x,y)$·Modulator$_i(x,y)$

4. The scatter corrected projection images are acquired by:

Sc_RawOb$_i(x,y)$=RawOb$_i(x,y)$−EstScOb$_i(x,y)$

Usually, after scatter correction, the noise within each scatter corrected projection image can be boosted up, and then special noise treatment can be used to address the boosted noise. In one exemplary embodiment, noise suppression for cone-beam reconstruction can be used to address or maintain the best spatial resolution while attaining the same noise level as methods commonly used in the related art noise suppression, such as a Hann window.

Exemplary Results

Figure 3A:
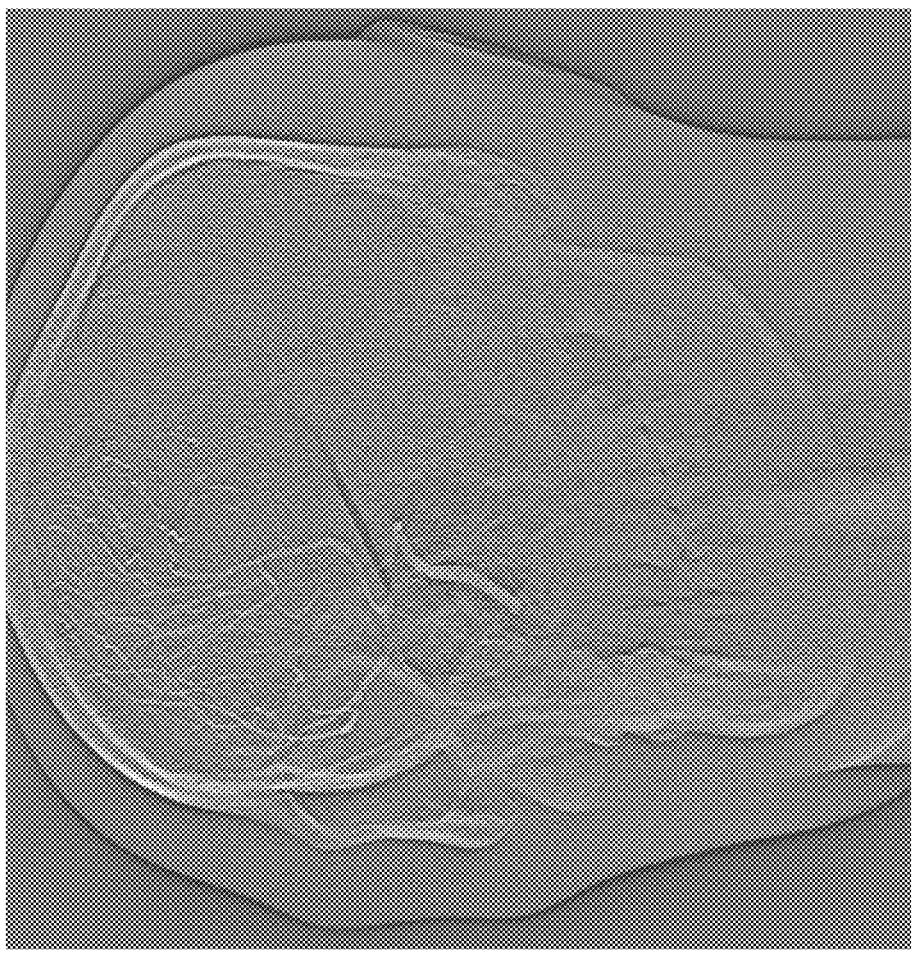
FIGS. 3A-3C are diagrams that show various exemplary head phantom projection images after ramp linear filtering.
Figure 3B:
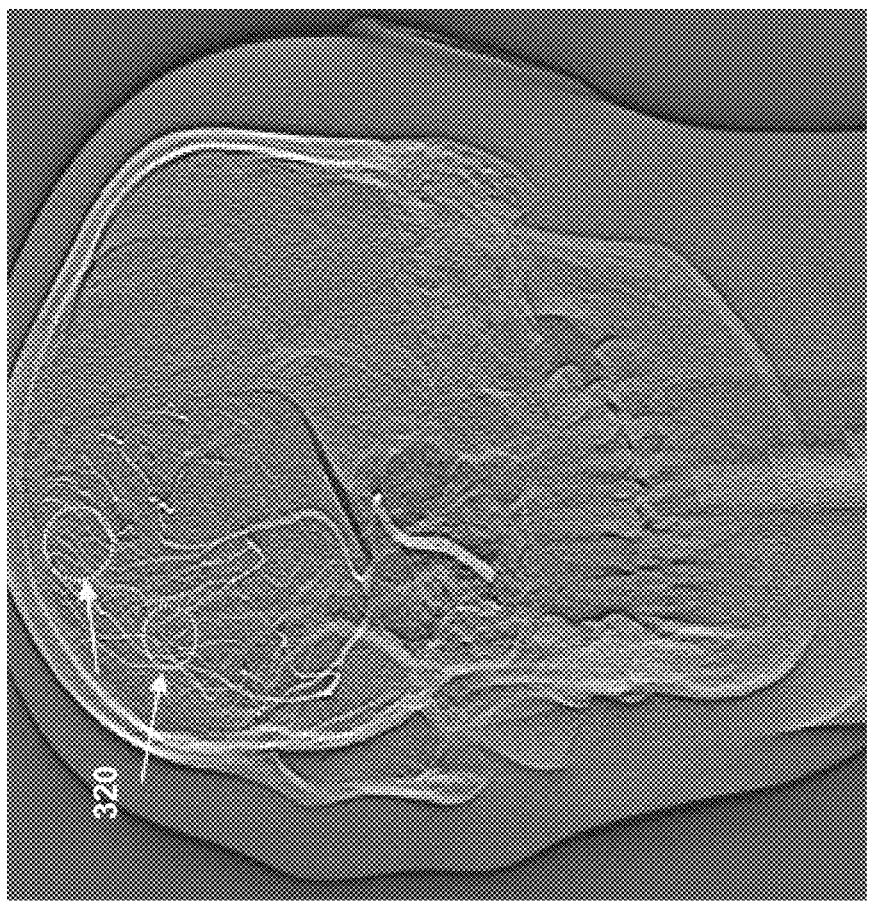
Figure 3C:
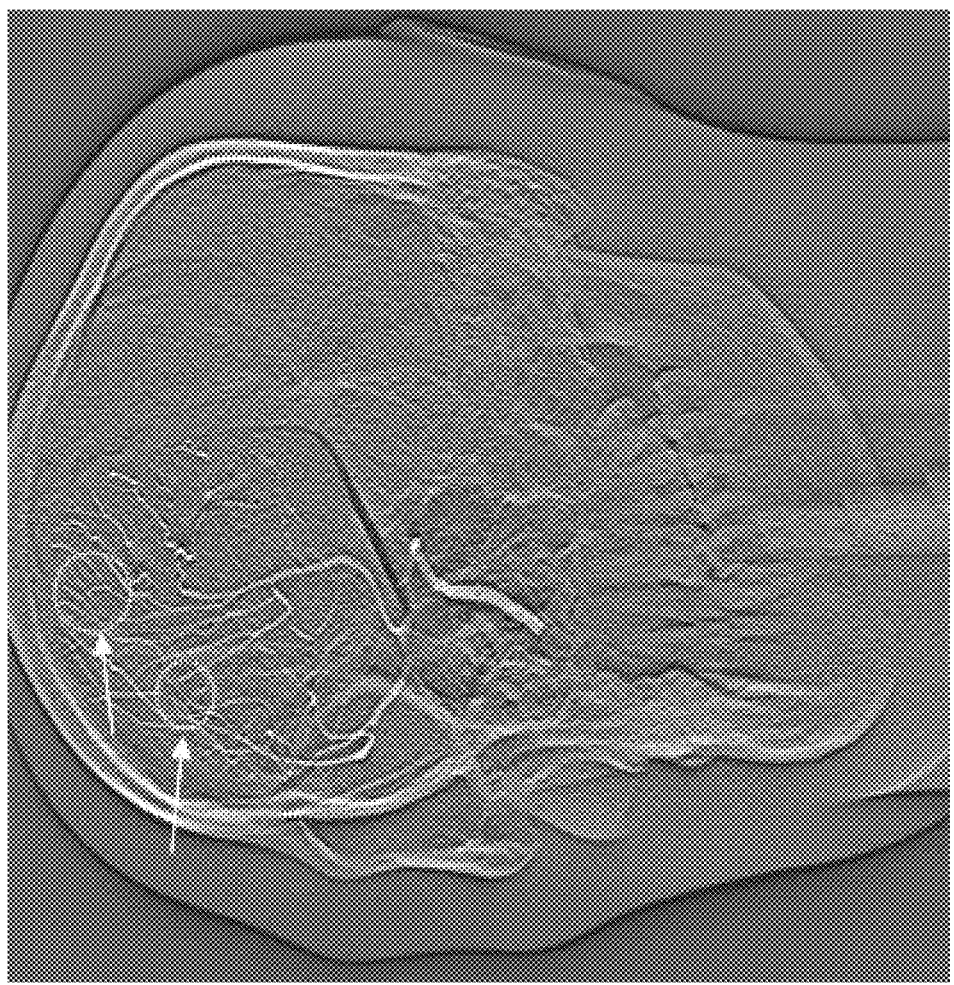

FIGS. 3A-3C are diagrams that show exemplary water insert cylinder phantom axial reconstructed images of a head phantom under different noise suppression. FIG. 3A is a diagram that shows an exemplary low contrast axial reconstructed image of a head phantom in log space after ramp linear row-wise filtering without noise suppression for the case of no anti-scatter grid and using no scatter correction. FIG. 3B is a diagram that shows an exemplary low contrast axial reconstructed image of the head phantom in log space after ramp linear row-wise filtering without noise suppression for the case of an anti-scatter grid. FIG. 3C is a diagram that shows an exemplary low contrast axial reconstructed projection image of the head phantom in log space after ramp linear row-wise filtering for the case of no anti-scatter grid and using an embodiment of scatter correction according to the application. In FIGS. 3A-3C, the same display window was applied to each of the images.

Figure 4B:
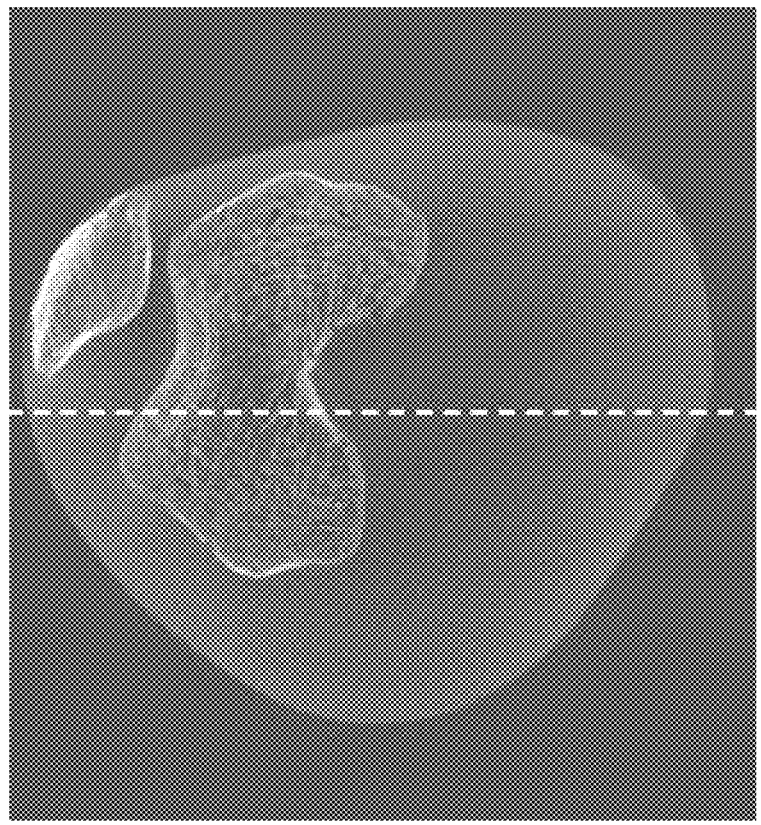

FIGS. 4A-4H are diagrams that show exemplary knee phantom axial and sagittal images, respectively, under different scatter correction scenarios. FIG. 4I is a diagram that shows image profile comparisons along the line shown in FIG. 4A, for the exemplary scatter correction scenarios. In FIGS. 4A-4H, the same display window was applied to each of the images.

Figure 4A:
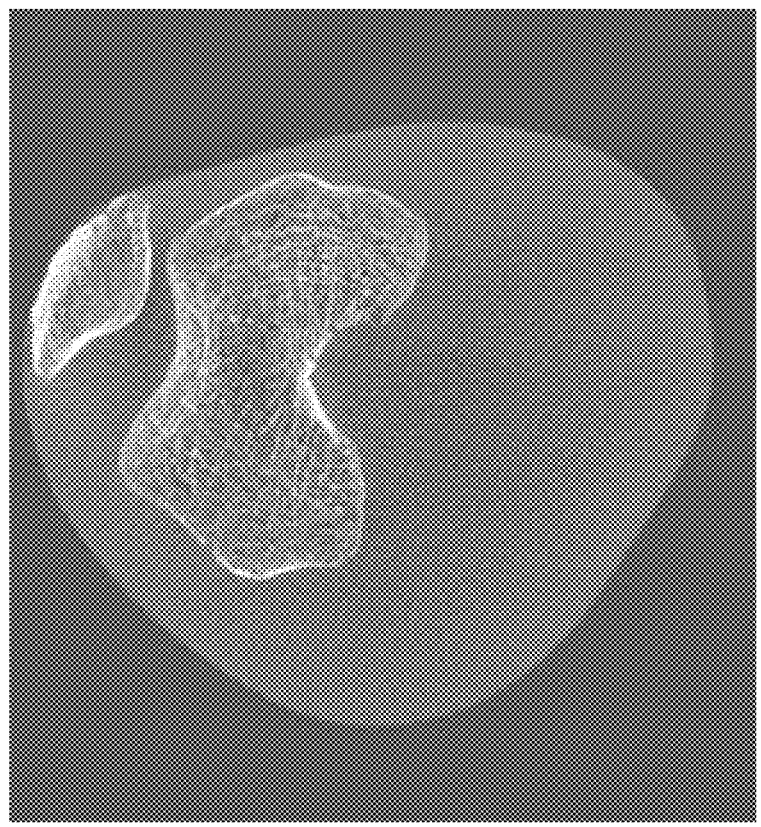
Figure 4C:
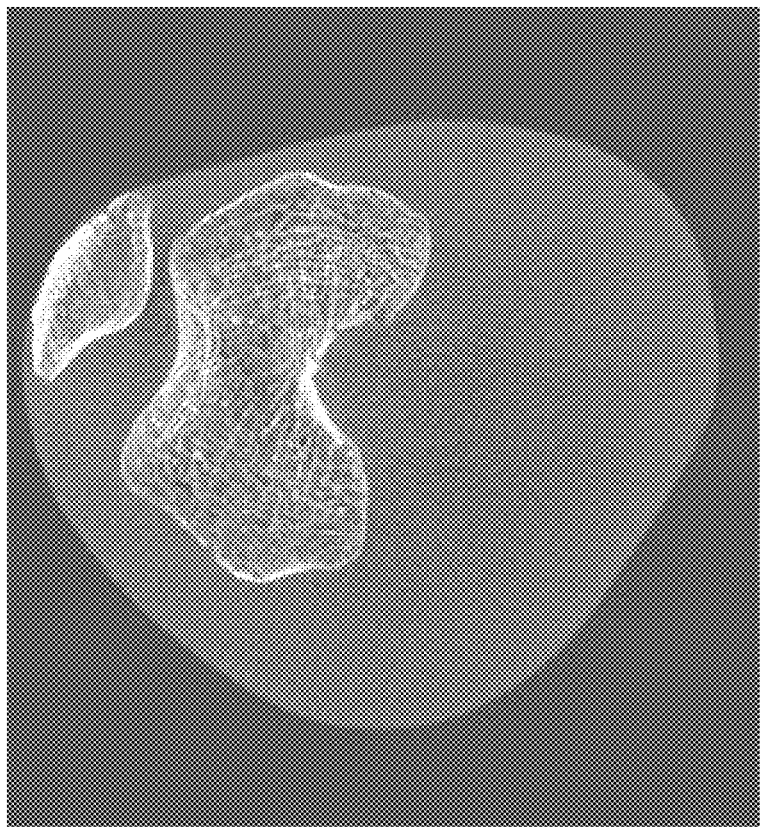
Figure 4D:
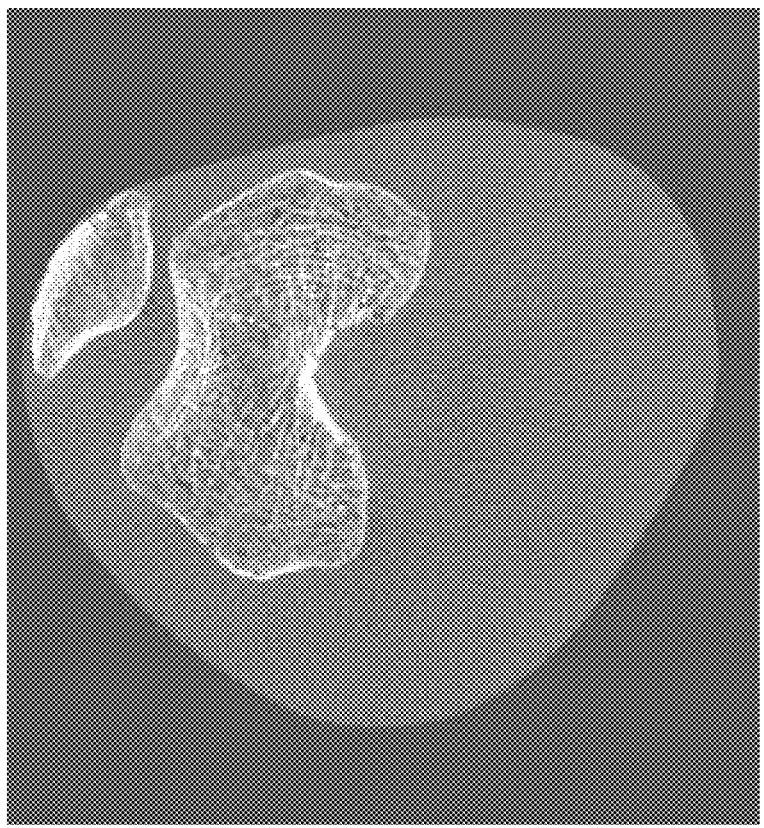

FIG. 4A is a diagram that shows an exemplary axial reconstructed image of a knee phantom for the case of no anti-scatter grid and using no scatter correction. FIG. 4B is a diagram that shows an exemplary axial reconstructed image of a knee phantom for the case using an anti-scatter grid and without scatter correction. FIG. 4C is a diagram that shows an exemplary axial reconstructed image of a knee phantom for the case of no anti-scatter grid and using an embodiment of scatter correction according to the application. FIG. 4D is a diagram that shows an exemplary axial reconstructed image of a knee phantom for the case of using an anti-scatter grid and using an embodiment of scatter correction according to the application.

Figure 4F:
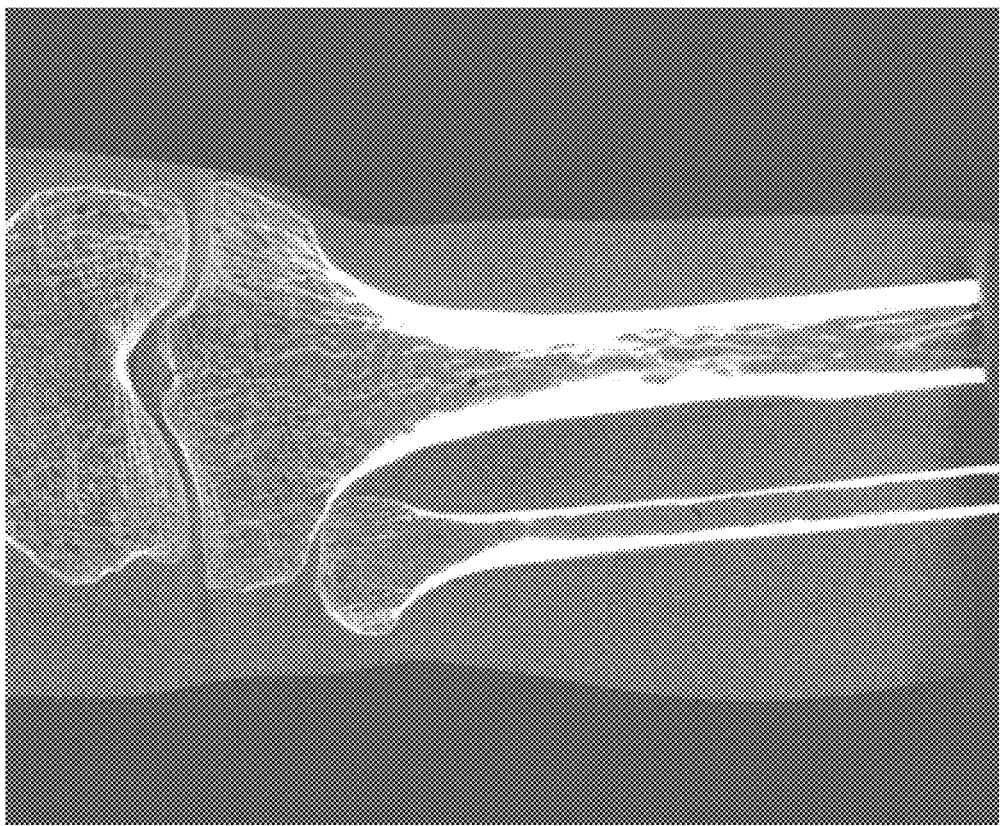
Figure 4E:
Figure 4I:
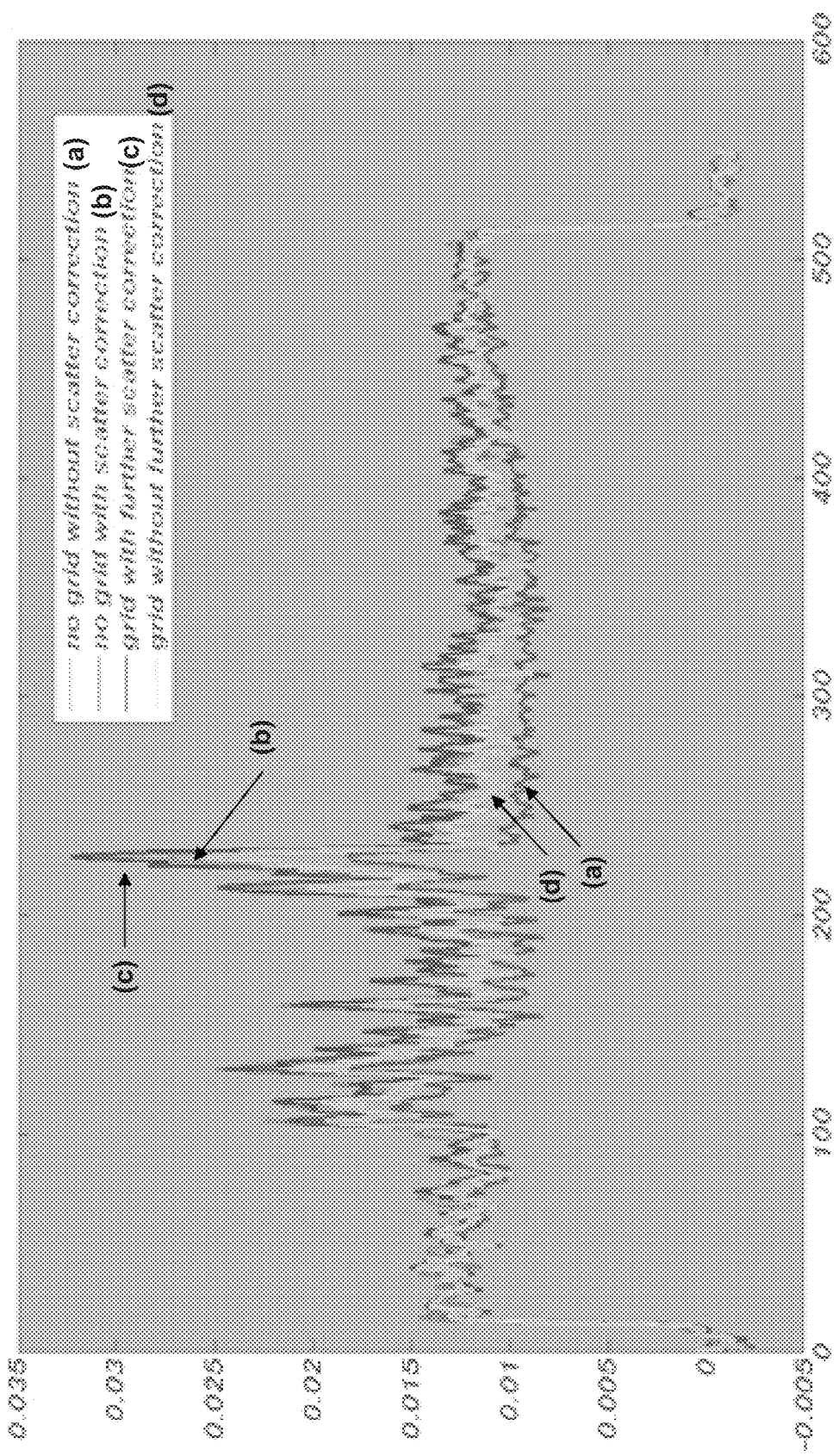
FIG. 4I is a diagram that shows image profile comparisons along the line shown in FIG. 4A, for the exemplary scatter correction scenarios.

FIG. 4E is a diagram that shows an exemplary coronal plane reconstructed image of a knee phantom for the case of no anti-scatter grid and using no scatter correction. FIG. 4F is a diagram that shows an exemplary coronal plane reconstructed image of a knee phantom for the case using an anti-scatter grid and without scatter correction. FIG. 4G is a diagram that shows an exemplary coronal plane reconstructed image of a knee phantom for the case of no anti-scatter grid and using an embodiment of scatter correction according to the application. FIG. 4H is a diagram that shows an exemplary sagittal plane reconstructed image of a knee phantom for the case of using an anti-scatter grid and using an embodiment of scatter correction according to the application.

Figure 5A:
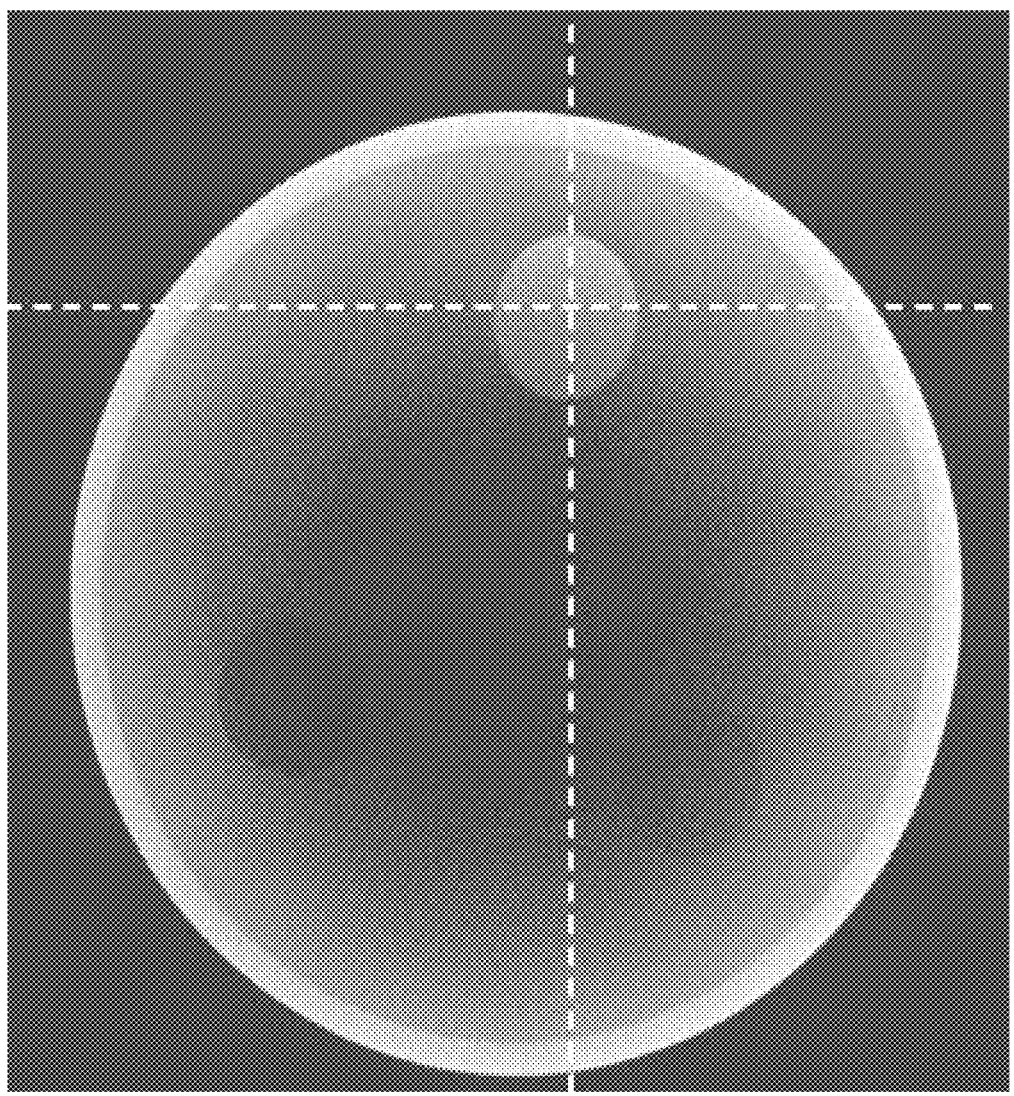
FIGS. 5A-5D are diagrams that show exemplary low contrast water insert cylinder phantom axial reconstructed images under different scatter correction scenarios.
Figure 5B:
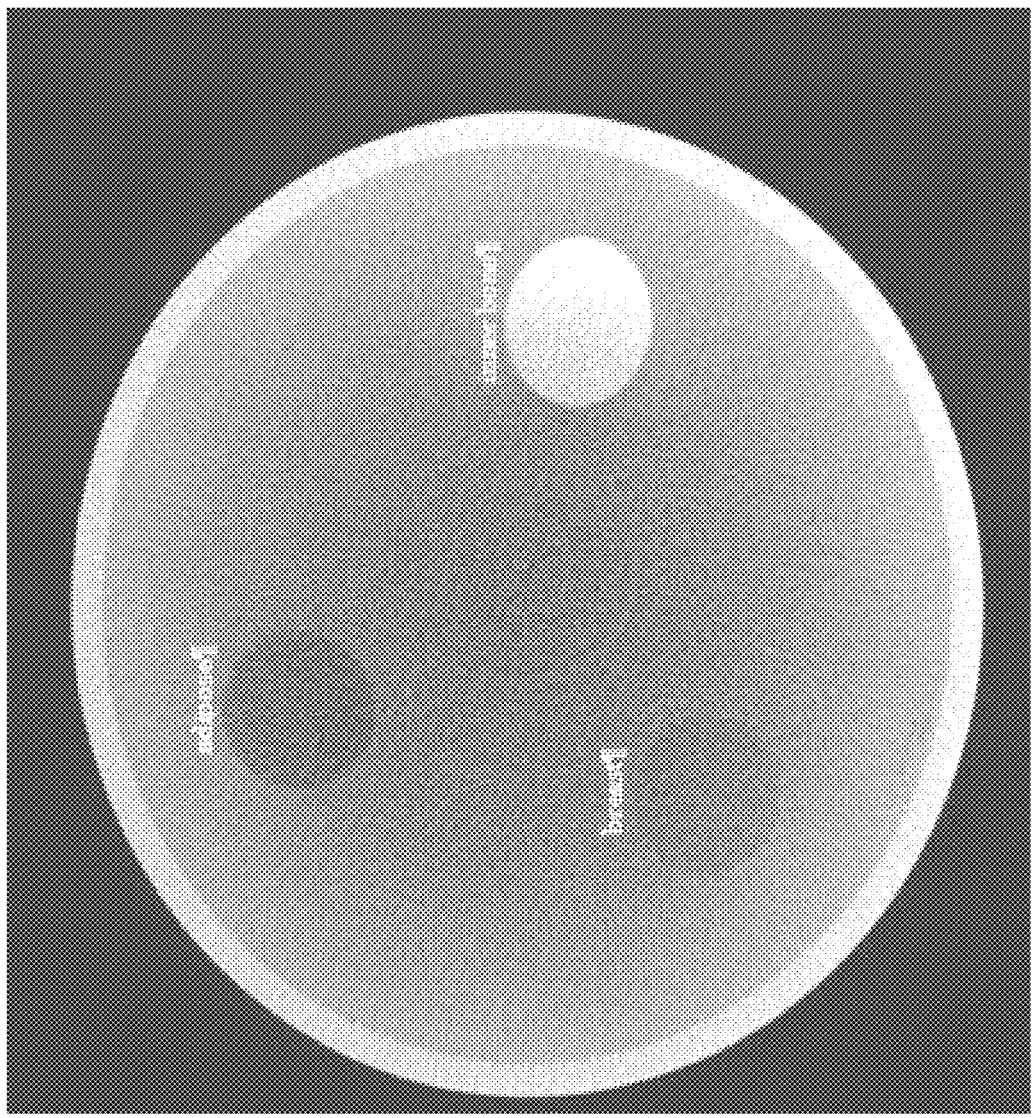
Figure 5C:
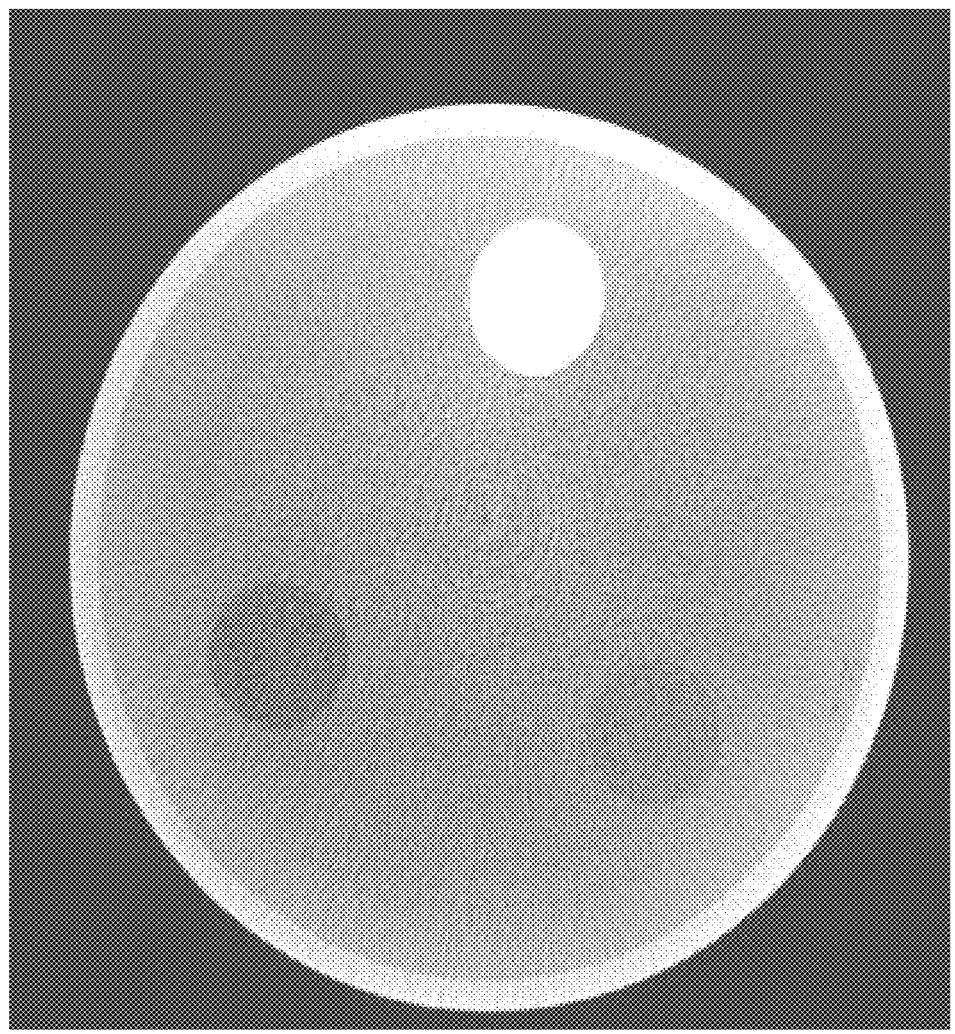
Figure 5D:
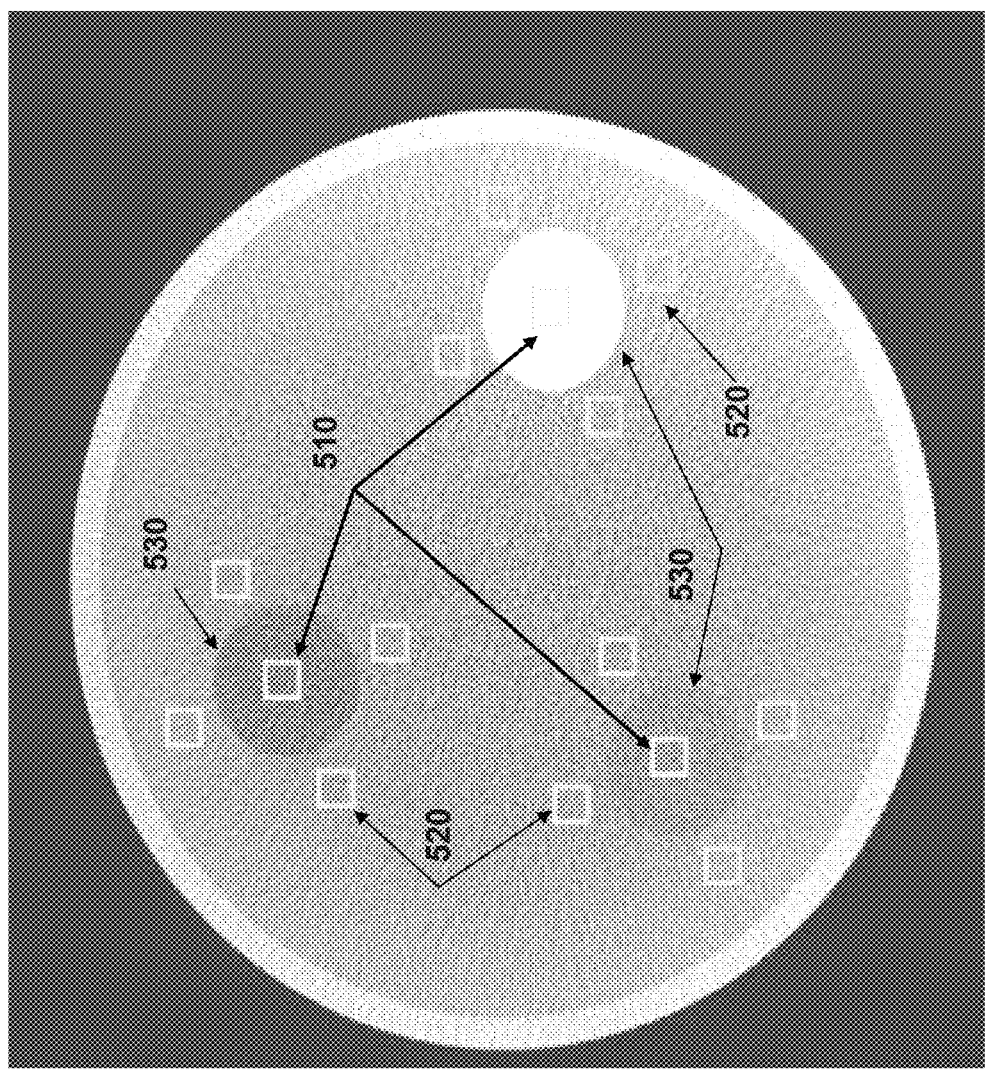
Figure 5E:
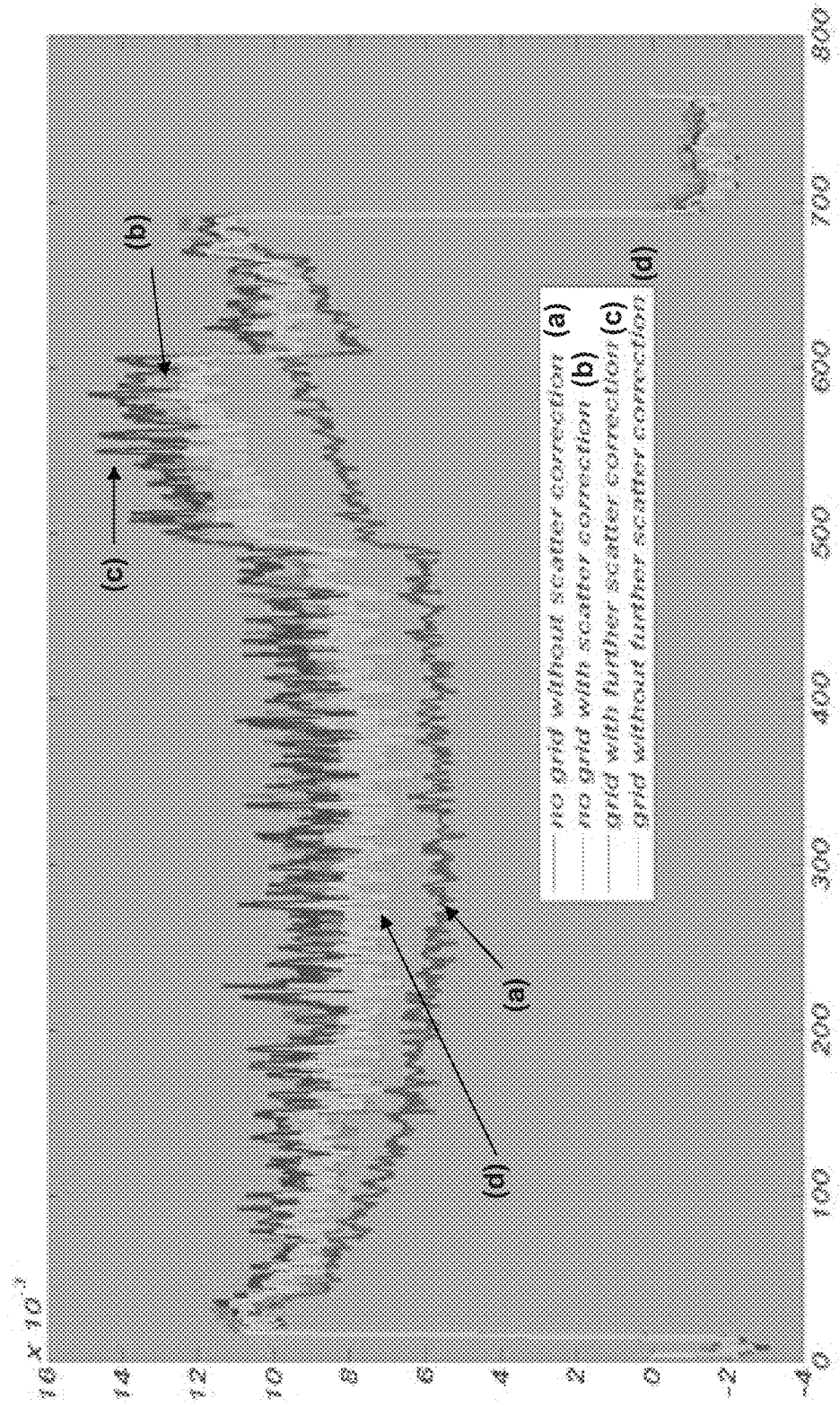
FIG. 5E is a diagram that shows image profile comparisons along the vertical line shown in FIG. 5A, for the exemplary scatter correction scenarios.

FIGS. 5A-5D are diagrams that show exemplary low contrast water insert cylinder phantom axial reconstructed images under different scatter correction scenarios. FIG. 5A is a diagram that shows an exemplary low contrast water insert cylinder phantom axial reconstructed image after linear row-wise filtering for the case of no anti-scatter grid and using no scatter correction. FIG. 5B is a diagram that shows an exemplary low contrast water insert cylinder phantom axial reconstructed image after linear row-wise filtering for the case of an anti-scatter grid and no scatter correction. FIG. 5C is a diagram that shows an exemplary low contrast water insert cylinder phantom axial reconstructed image after linear row-wise filtering for the case of no anti-scatter grid and using an embodiment of scatter correction according to the application. FIG. 5D is a diagram that shows an exemplary low contrast water insert cylinder phantom axial reconstructed image after linear row-wise filtering for the case of using an anti-scatter grid and using an embodiment of scatter correction according to the application. FIG. 5E is a diagram that shows image profile comparisons along the vertical line shown in FIG. 5A, for the exemplary scatter correction scenarios. In FIGS. 5A-5D, the same display window was applied to each of the images.

Figure 6A:
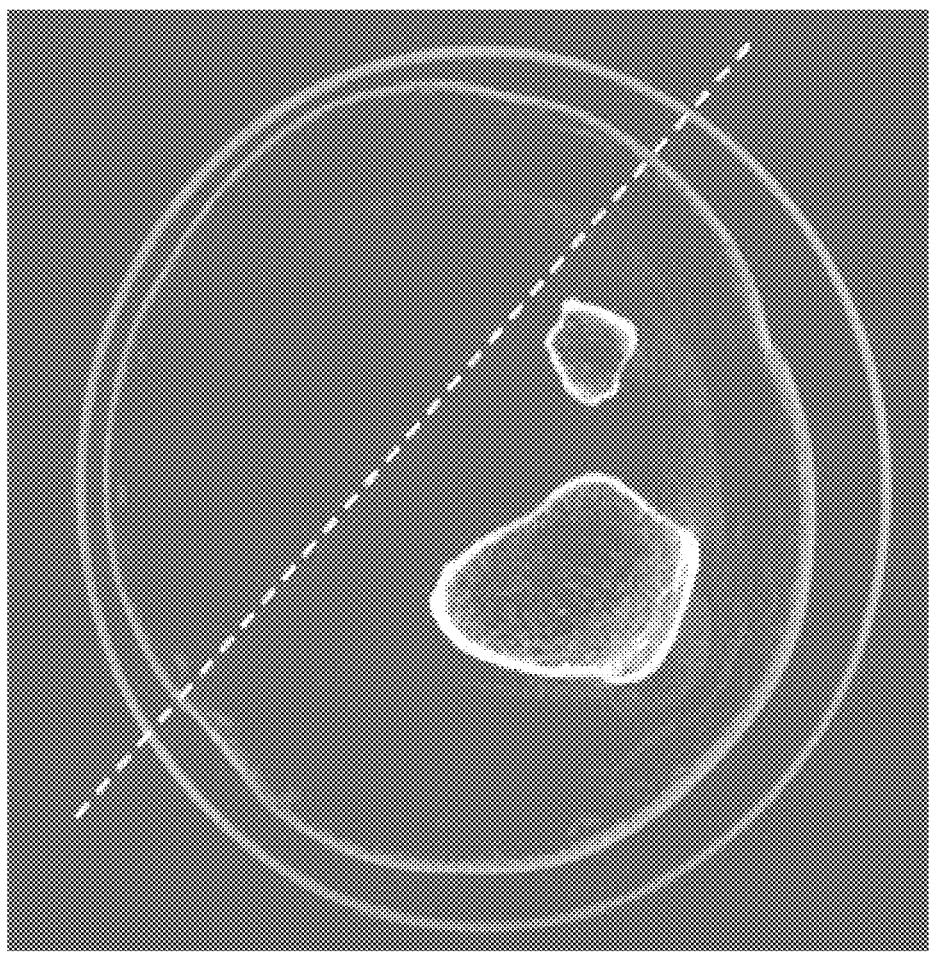
FIGS. 6A-6C and 6E-6G are diagrams that show exemplary knee cadaver axial and sagittal sectional images, respectively, under different scatter correction scenarios.
Figure 6B:
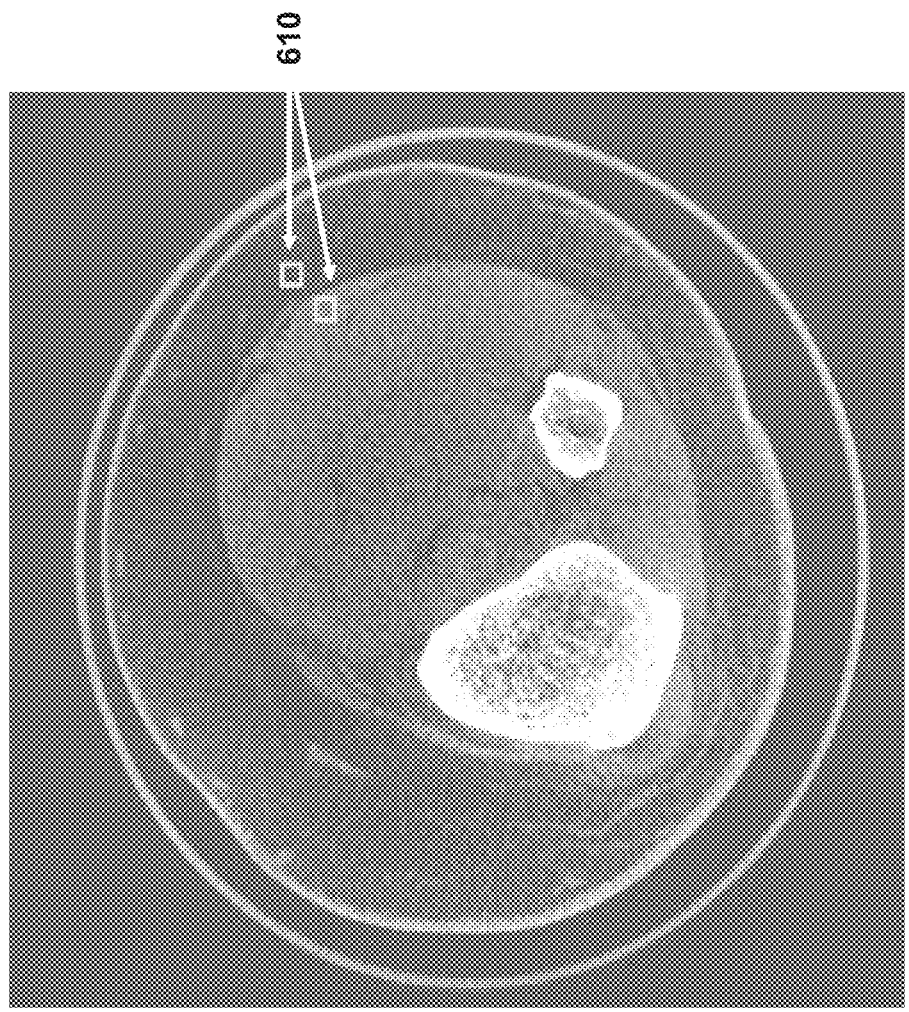
Figure 6C:
Figure 6D:
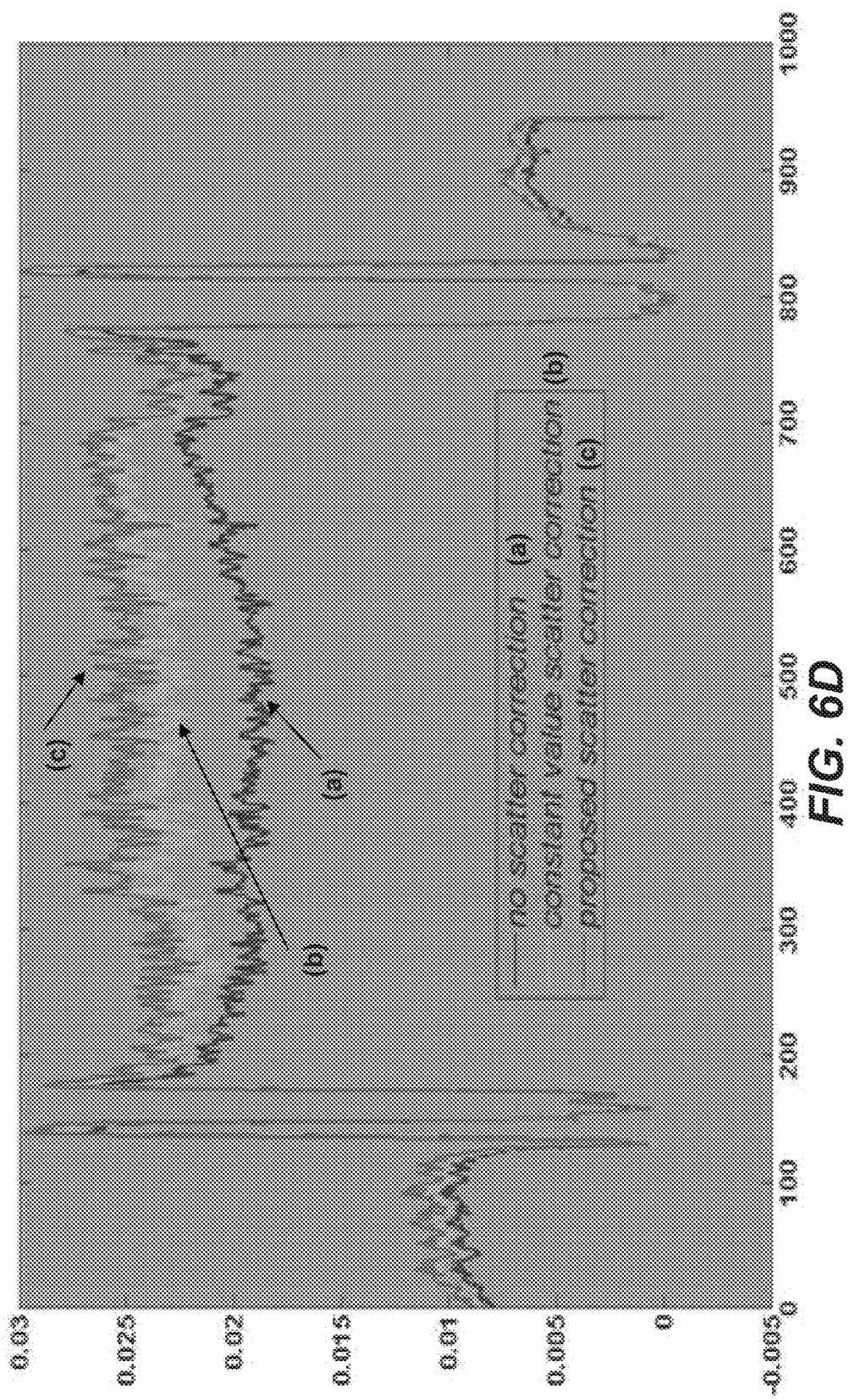
FIG. 6D is a diagram that shows image profile comparisons along the line shown in FIG. 6A, for the exemplary scatter correction scenarios.

FIG. 6A is a diagram that shows an exemplary axial reconstructed image of a knee cadaver for the case of no anti-scatter grid and using no scatter correction. FIG. 6B is a diagram that shows an exemplary axial reconstructed image of a knee cadaver for the case using no anti-scatter grid and constant scatter correction. FIG. 6C is a diagram that shows an exemplary axial reconstructed image of a knee cadaver for the case of no anti-scatter grid and using an embodiment of scatter correction according to the application. FIG. 6D is a diagram that shows image profile comparisons along the line shown in FIG. 6A, for the exemplary scatter correction scenarios.

Figure 6E:
Figure 6G:
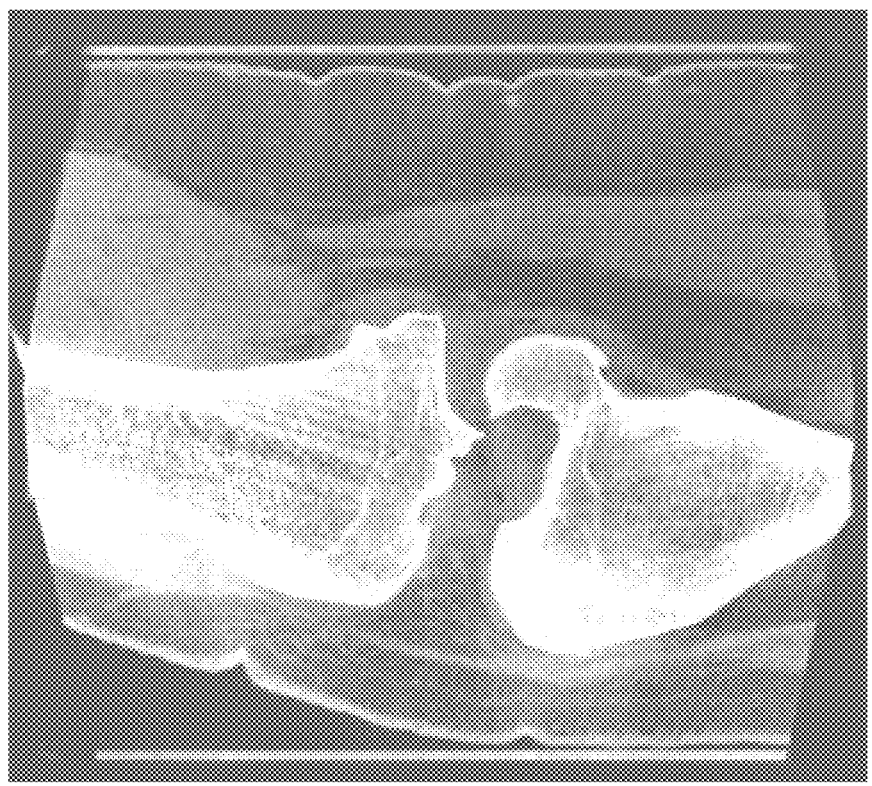
Figure 6F:
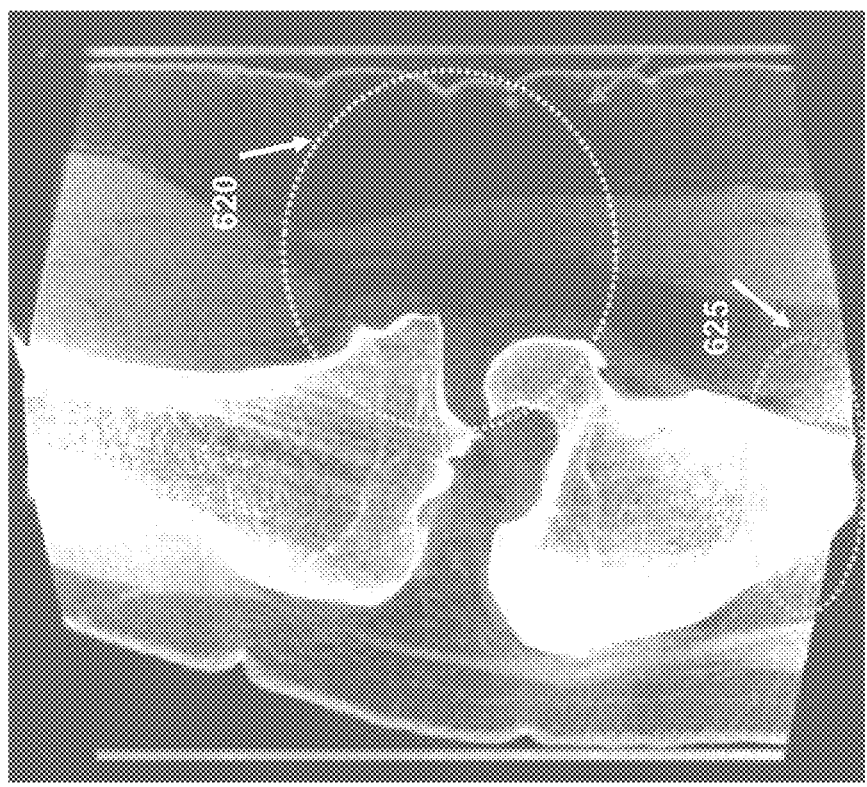

FIG. 6E is a diagram that shows an exemplary sagittal image of a knee cadaver for the case of no anti-scatter grid and using no scatter correction. FIG. 6F is a diagram that shows an exemplary sagittal image of a knee cadaver for the case using no anti-scatter grid and constant scatter correction. FIG. 6G is a diagram that shows an exemplary sagittal image of a knee cadaver for the case of no anti-scatter grid and using an embodiment of scatter correction according to the application. Images shown in FIGS. 6A-6C and 6E-6G are shown with the same display window level and width.

The contrast to noise was evaluated using the square boxes having an exemplary box size of 25 pixels by 25 pixels as shown in FIG. 5D. The evaluation was conducted on adipose, breast and inner bone inserts and corresponding surrounding background. The displacement of those square boxes within and outside the inserts was set up trying to reduce or eliminate the affection of the cupping effect on the noise evaluation in the background. Standard deviation (STD) of the background was also evaluated by taking the averaging of four square boxes. The CNR was calculated through dividing the background STD by the contrast between three inserts and their background. Exemplary results are summarized in Table 1 shown below.

TABLE 1

Contrast to noise ratio among different scenarios

|  | No_grid (no correction) | No_grid (correction) | grid (no correction) | grid (correction) |
| --- | --- | --- | --- | --- |
| CNR (adipose) | 2.13 | 1.77 | 1.79 | 1.91 |
| CNR (breast) | 1.61 | 0.98 | 1.16 | 0.93 |
| CNR (inner bone) | 3.49 | 5.25 | 4.97 | 4.80 |

A contrast to noise ratio evaluation was also conducted on one of the raw projection images in linear space to determine whether using an anti-scatter grid or not using an anti-scatter grid would significantly impact a CNR for each of these inserts. An exemplary 10 by 10 pixel square box is used to make the measurements. One box is placed in the center of the insert to measure the mean value of the signal. Four boxes are used for background mean value and noise measurement. Two boxes are placed on each side of the insert during evaluation. Each of these two boxes on the same side is placed close to each other in order to eliminate the perturbation caused by different x-ray path lengths. Exemplary results are summarized in Table 2 shown below.

TABLE 2

Contrast to noise ratio of the inserts in linear space among no grid and grid scenarios

| CNR | No Grid Case | Grid Case |
| --- | --- | --- |
| Adipose | 2.72 | 1.77 |
| Breast | 1.5 | 1.32 |
| Inner Bone | 7.47 | 6.79 |

Another CNR evaluation was conducted for three image processing scenarios by taking the difference between muscle and background, which was then divided by the standard deviation of the background. Exemplary boxes 610 (e.g., 10 by 10 pixel square) used for this evaluation are shown in FIG. 6B. Exemplary results are summarized in Table 3 shown below.

TABLE 3

Contrast to noise ratio among different scenarios

|  | No_grid (no correction) | No_grid (constant value of 300 for correction) | No grid (proposed correction) |
| --- | --- | --- | --- |
| CNR | 8.18 | 8.90 | 10.51 |

Use of an anti-scatter grid has various disadvantages. For example, the attenuation of the anti-scatter grid on the primary X-ray beam can be up to at least 30 percent. Further, the possible loss of the spatial resolution can result when the anti-scatter grid is employed, (e.g., see FIG. 3B in the circled area 320 and FIG. 3C, where some tiny blood vessel structures can not be resolved in FIG. 3B). The same phenomenon happened in Knee phantom image scanned on extremity CBCT system embodiment, as was shown and FIG. 4H in the yellow circled area 410 in FIG. 4G and in the yellow circled area 420 in FIG. 4H, trabecular bone structure is more delineated in no grid case of FIG. 4G than in the grid case of FIG. 4H. The visualization of the knee phantom study showed that scatter correction embodiments described herein without using anti-scatter grid, can achieve about the same level of scatter correction as when the anti-scatter grid is employed combined with same scatter correction scheme. The contrast to noise ratio (CNR) evaluation conducted on the projection image showed that using the grid does not improve the CNR for all three inserts being used, adipose, breast and inner bone. CNR evaluation on reconstructed data also follow the same study on projection data except for the insert of inner bone, in which the CNR with grid is larger than that without grid. The same scatter correction scheme applied on either grid or non-grid case does not improve the CNR for low contrast objects, adipose and breast, again except for the higher contrast object, inner bone, where the CNR gets improved for the case of no grid is used. For the case where grid is used, CNR dropped when an embodiment of scatter correction scheme is conducted.

Knee cadaver study indicated that an embodiment of a scatter correction scheme works well without scatter grid in terms of uniformity in an axial the image view. Constant value based scatter correction works in a very limited way, and thus, the constant value based scatter correction can over-correct and under-correct the images contaminated with scatter. As shown in FIG. 6F, there are two ellipsoids in the image, the bigger ellipsoid 620 shows that the constant correction of 300 under-correct the image and smaller one 625 shows the constant correction of 300 over-correction. The rough CNR evaluation on the cadaver knee imaging images shows that more than two times bigger than that of without scatter correction can be achieved with an embodiment of a scatter correction scheme, while cupping effect can be largely reduced indicating more accurate CT number associated with different materials are produced in the reconstructed images.

One rationale upon which certain exemplary scatter correction embodiments were built seems to be consistent with the observed phenomenon based on phantom studies and/or on the cadaver data. Based on evaluation through CNR on water phantom with inserts, it is indicated that grid would not improve the CNR for low contrast objects on CBCT prototype system under the current X-ray exposing parameter, the only benefit of using grid is to improve the uniformity and get more accurate CT number of the objects across the imaging field of view, which can also be achieved through at least one scatter correction embodiment when no grid is employed. Since scattering always increases with the increase of the X-ray output fluency determined by mAs and/or energy and combined with the consideration of the loss of the resolution of some tiny structures when grid is employed that was demonstrated by the head phantom projection images as well as by the knee phantom study. For at least one embodiment, a scatter correction scheme should be parameter-adapted to this practical scenario.

It is desirable to maintain clinically acceptable diagnostic imaging in the digital radiographic image domain preferably while maintaining or reducing radiographic exposure levels. Embodiments of systems and methods according to the application can provide a CBCT imaging apparatus with a scatter correction capability and/or methods for scatter correction for digital radiographic imaging. Certain exemplary embodiments of radiographic imaging apparatus and/or methods according to the application can better characterize scatter within projection data over a range of scan angles and/or within a shadow of an object. In one embodiment, CBCT imaging apparatus and/or methods achieve scatter correction where imaging using an anti-scatter grid is not available (e.g., dose, geometry).

In one embodiment, a plurality of 2D projection data can be down sampled prior to provide down sampled data and/or an image that can be used in accordance with system and/or method embodiments herein.

Exemplary embodiments described herein take a novel approach to scatter correction procedures by processing the projection data prior to reconstruction processing for 3D volume image reconstruction.

Referring to the logic flow diagram of FIG. 7A, there is shown an image processing sequence S700 according to an embodiment of the application. Steps S110, S120, S130, S140, S150, S160, in this sequence are the same steps described earlier for the conventional sequence of FIG. 2. In this exemplary sequence, a scatter correction process (e.g., operation block 720, indicated in dashed outline in FIG. 7A), can follows image correction step S130 and can input raw 2D image data and output scatter corrected raw 2D image data. In one embodiment, the correction can be conducted using the projection information in S130 and projection information after S140.

Figure 7B:
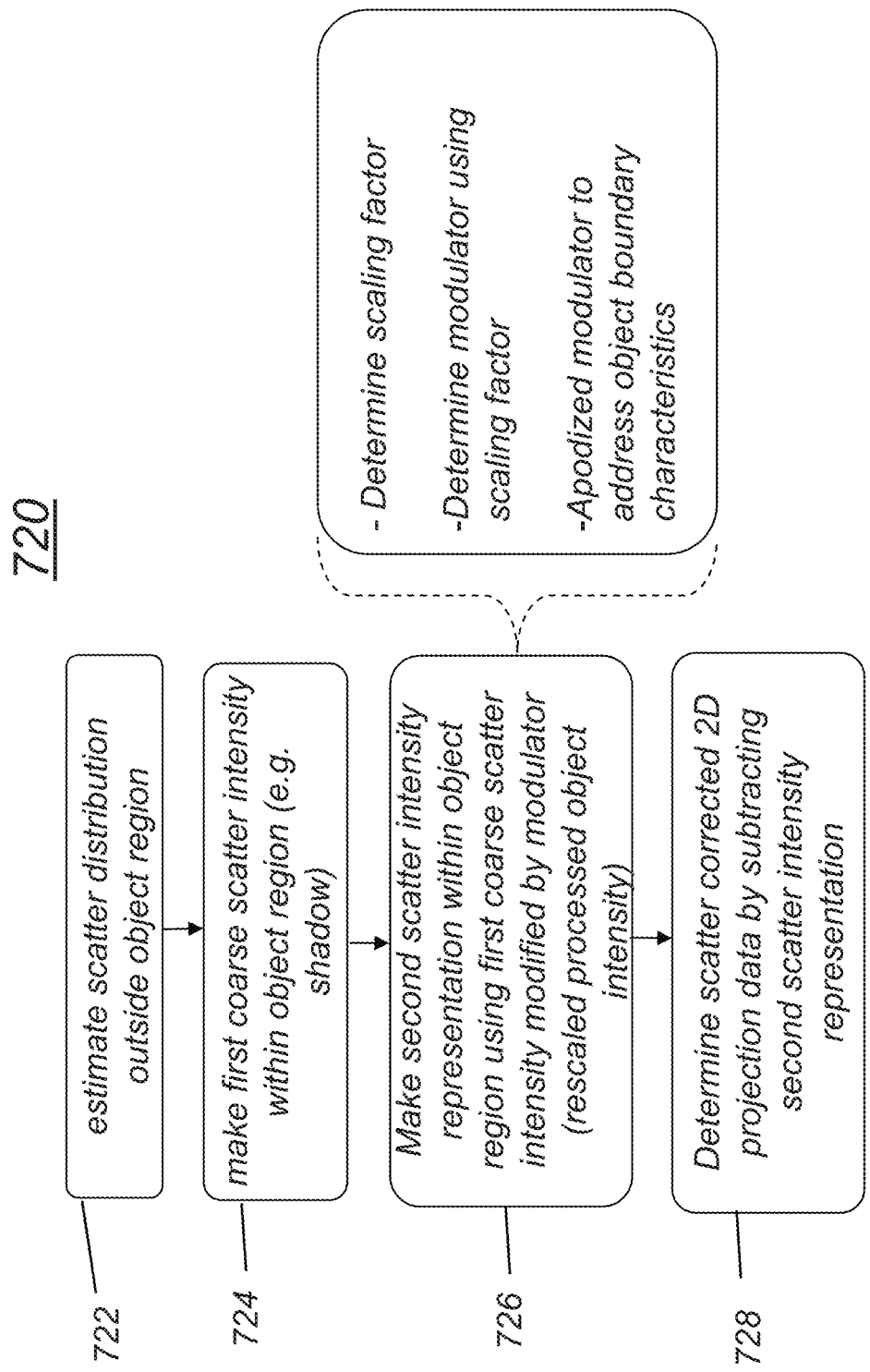

As shown in FIG. 7B, when a scatter correction imaging sequence or scatter correction mode is selected, the raw 2D image data (e.g., from a FPD) can be processed by a scatter correction process. As shown in FIG. 7B, the operation block 720 can begin by processing input raw 2D image data that can include a plurality of 2D projection data to determine values for a scatter distribution outside an object region (e.g., Io) and the projection data can be divided to determine a region of object shadow (operation block 724). In one embodiment, an exemplary value for Io can be determined ahead of time (e.g., for a plurality of x-ray source beam energies). Then, a first (e.g., coarse) scatter intensity estimation can be determined for the region of object shadow (operation block 724) using the values for a scatter outside the object region (e.g., from operation block 722). In operation block 726, a modulation function to modify the first scatter intensity distribution can be determined. The modulation function can be determined by (a) determining a scaling factor, and (b) using the scaling factor to determine the modulation function. The modulation function can preferably be estimated as a function from log space to estimate scatter intensity (e.g., in contrast to using an object's geometry). In one embodiment, the scaling factor can be determined by identifying a selected point of the exposure sequence such as a point of greatest attenuation in the entire exposure sequence and at that selected point also using a scatter/primary ratio (spr) to generate the scaling factor. The scaling factor can be used to generate a modulation function that can be applied for each of the plurality of projection data (e.g. 2D projection data) in an exposure sequence. In one embodiment, the modulation function can be rescaled processed object intensity. Further, the modulation function can be optionally adjusted to address boundary conditions, for example by dampening or weighting from a peak to each opposite endpoints in a line/row of data, which can compensate scatter correction at boundary conditions.

In operation block 728, scatter corrected 2D projection data can be determined by combining (e.g., subtracting) the second scatter intensity distribution from the input raw 2D image data. From operation block 728, processing can jump back to image correction step S130 or the logarithmic operation step S140.

Although described herein with respect to CBCT digital radiography systems, embodiments of the application are not intended to be so limited. For example, other DR imaging system such as dental DR imaging systems, mobile DR imaging systems or room-based DR imaging systems can utilize method and apparatus embodiments according to the application. As described herein, an exemplary flat panel DR detector/imager is capable of both single shot (radiographic) and continuous (fluoroscopic) image acquisition. Further, a fan beam CT DR imaging system can be used.

DR detectors can be classified into the "direct conversion type" one for directly converting the radiation to an electronic signal and the "indirect conversion type" one for converting the radiation to fluorescence to convert the fluorescence to an electronic signal. An indirect conversion type radiographic detector generally includes a scintillator for receiving the radiation to generate fluorescence with the strength in accordance with the amount of the radiation.

Cone beam CT for weight-bearing knee imaging as well as for other extremities is a promising imaging tool for diagnosis, preoperative planning and therapy assessment.

It should be noted that the present teachings are not intended to be limited in scope to the embodiments illustrated in the figures.

As used herein, controller/CPU for the detector panel (e.g., detector 24, FPD) or imaging system (controller 30 or detector controller) also includes an operating system (not shown) that is stored on the computer-accessible media RAM, ROM, and mass storage device, and is executed by processor. Examples are not limited to any particular operating system, however, and the construction and use of such operating systems are well known within the art. Embodiments of controller/CPU for the detector (e.g., detector 24) or imaging system (controller 30) are not limited to any type of computer or computer-readable medium/computer-accessible medium (e.g., magnetic, electronic, optical). The construction and operation of such computers are well known within the art. The controller/CPU can be operated using at least one operating system to provide a graphical user interface (GUI) including a user-controllable pointer. The controller/CPU can have at least one web browser application program executing within at least one operating system, to permit users of the controller/CPU to access an intranet, extranet or Internet world-wide-web pages as addressed by Universal Resource Locator (URL) addresses.

In addition, while a particular feature of an embodiment has been disclosed with respect to only one of several implementations or embodiments, such feature can be combined with one or more other features of the other implementations and/or other exemplary embodiments as can be desired and advantageous for any given or particular function. To the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. Further, in the discussion and claims herein, the term "exemplary" indicates the description is used as an example, rather than implying that it is an ideal.

The invention has been described in detail with particular reference to exemplary embodiments, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A computer implemented method comprising:
    capturing an image of an object using an x-ray source emitting x-rays toward the object and a detector capturing image data of the object;
    modifying the captured image to correct artifacts therein caused by scattering of the x-rays, the step of modifying the image including:
        determining a scatter distribution of the x-rays in an air region near the object using the captured image of the object;
        estimating a scatter intensity of the x-rays within the object based on the determined scatter distribution; and
        subtracting the estimated scatter intensity of the x-rays from the captured image to provide the modified image.

2. The computer implemented method of claim 1, further comprising:
    modulating the estimated scatter intensity of the x-rays based on a modulator, and determining the modulator as a function of an inverted scaled image value; and
    determining the inverted scaled image value as a function of a scaling factor.

3. The computer implemented method of claim 2, further comprising:
    converting the captured image data of the object into corresponding image data in log space;
    searching for a highest intensity image datum in the log space across all the image data;
    determining a scatter-to-primary ratio based on the highest intensity image datum; and
    determining the scaling factor as a function of the scatter-to-primary ratio, the image data in the log space, the captured image data of the object, and the estimated scatter intensity of the x-rays within the object.

4. The computer implemented method of claim 3, wherein the step of determining the scaling factor includes determining the scaling factor from the captured image of the object, and the step of determining the inverted scaled image value includes dividing the image data in log space by the scaling factor.

5. The computer implemented method of claim 1, wherein the step of estimating the scatter intensity of the x-rays within the object includes performing a linear interpolation of the determined scatter distribution of the x-rays in the air region near the object.

6. The computer implemented method of claim 5, wherein the step of determining the scatter distribution of the x-rays in the air region near the object includes determining the scatter distribution of the x-rays in an air gap between the x-ray source and the object.

7. The computer implemented method of claim 6, further comprising capturing a plurality of images of the object, wherein the step of determining the scatter distribution of the x-rays in an air gap between the x-ray source and the object is performed for each of the captured images of the object.

8. The computer implemented method of claim 2, wherein a magnitude of the modulator is proportional to a percentage of scattered x-rays within the object.

9. The computer implemented method of claim 1, further comprising capturing a plurality of images of the object and performing the step of modifying on each of the captured plurality of images, including processing the plurality of the modified images to reconstruct a 3D volume image of the object, storing the 3D volume image of the object in a computer accessible memory, and displaying the 3D volume image.

10. In a method of image processing of a radiographic digital image of a subject, executed at least in part on a computer, the improvement comprising:
    modifying the radiographic digital image to correct artifacts in the image caused by scattering of x-rays, the step of modifying including:
        determining a scatter distribution of the xrays in an air region near the subject using the radiographic digital image of the subject;
        estimating a scatter intensity of the x-rays within the subject based on the determined scatter distribution; and
        subtracting the estimated scatter intensity of the x-rays from the radiographic digital image to provide the modified radiographic digital image.

11. The method of claim 10, further comprising:
    converting the image of the subject into corresponding image data in log space;
    searching for a highest intensity image datum in the log space;
    determining a scatter-to-primary ratio based on the highest intensity image datum; and
    processing the image of the subject as a function of the scatter-to-primary ratio, the image data in the log space, and the estimated scatter intensity of the x-rays within the subject.

12. The method of claim 10, wherein the step of estimating the scatter intensity of the x-rays within the subject includes performing a linear interpolation of the determined scatter distribution of the x-rays in the air region near the subject.

13. The method of claim 12, further comprising modifying a plurality radiographic digital images of the subject, wherein the step of determining the scatter distribution is performed for each of the plurality of radiographic digital images of the subject.

14. The method of claim 13, further comprising processing the plurality of the radiographic digital images of the subject to reconstruct a 3D volume image of the subject, storing the 3D volume image of the subject in a computer accessible memory, and displaying the 3D volume image of the subject.

15. A computer implemented method comprising:
capturing an image of an object using an x-ray source emitting x-rays toward the object and a detector capturing image data of the object;
modifying the captured x-ray image to correct artifacts in the image caused by scattering of the x-rays, the step of modifying the image including:
determining a scatter distribution of the x-rays in an air region near the object;
determining a first scatter intensity of the x-rays within a shadow of the object based on the determined scatter distribution;
determining a final scatter intensity of the x-rays within the shadow of the object, including modulating the first scatter intensity of the x-rays based on a modulator; and
subtracting the determined final scatter intensity of the x-rays from the captured x-ray image to provide the modified x-ray image.

16. The computer implemented method of claim 15, further comprising:
determining the modulator as a function of an inverted scaled image value; and
determining the inverted scaled image value as a function of a scaling factor.

17. The computer implemented method of claim 16, further comprising:
converting the captured image data of the object into corresponding image data in log space;
searching for a highest intensity image datum in the log space across the image data of the object;
determining a scatter-to-primary ratio based on the highest intensity image datum; and
determining the scaling factor as a function of the scatter-to-primary ratio, the captured image data in the log space, the captured image data of the object, and the first scatter intensity of the x-rays within the shadow of the object.

18. The computer implemented method of claim 17, wherein the step of determining the scaling factor includes determining the scaling factor from the captured image of the object, and the step of determining the inverted scaled image value includes dividing the image data in log space by the scaling factor.

19. The computer implemented method of claim 15, wherein the step of determining the first scatter intensity of the x-rays within the shadow of the object includes performing a linear interpolation of the determined scatter distribution of the x-rays in the air region near the object.

20. The computer implemented method of claim 19, wherein the step of determining the scatter distribution of the x-rays in the air region near the object includes determining the scatter distribution of the x-rays in an air gap between the x-rays source and the object.

21. The computer implemented method of claim 15, wherein a magnitude of the modulator is proportional to a percentage of scattered x-rays within the shadow of the object.

22. In a method of digital radiographic image processing of an image of a subject, executed at least in part on a computer, the improvement comprising:
modifying the radiographic image of the subject to correct artifacts in the image caused by scattering of x-rays, the step of modifying the image including:
determining a scatter distribution of the x-rays in an air region near the subject;
determining a first scatter intensity of the x-rays within a shadow of the subject based on the determined scatter distribution;
determining a final scatter intensity of the x-rays within the shadow of the subject; and
subtracting the determined final scatter intensity of the x-rays from the radiographic image of the subject to provide the modified radiographic image of the subject.

23. The method of claim 22, further comprising:
converting the captured radiographic image of the subject into corresponding image data in log space;
searching for a highest intensity image datum in the log space;
determining a scatter-to-primary ratio based on the highest intensity image datum; and
processing the captured radiographic image of the subject as a function of the scatter-to-primary ratio, the captured image data converted into the log space, and the first scatter intensity of the x-rays within the shadow of the subject to provide the modified radiographic image of the subject.

24. The computer implemented method of claim 22, wherein the step of determining the first scatter intensity of the x-rays within the shadow of the subject includes performing a linear interpolation of the determined scatter distribution of the x-rays in the air region near the subject.

* * * * *